(12) United States Patent
Rosemberg

(10) Patent No.: US 8,343,147 B2
(45) Date of Patent: Jan. 1, 2013

(54) ELECTROLYTIC TISSUE TREATMENT

(75) Inventor: Yossef Rosemberg, Raanana (IL)

(73) Assignee: EC Point Medical, Inc., Henderson, NV (US)

( * ) Notice: Subject to any disclaimer, the term of this patent is extended or adjusted under 35 U.S.C. 154(b) by 640 days.

(21) Appl. No.: 12/446,969

(22) PCT Filed: Oct. 23, 2007

(86) PCT No.: PCT/US2007/082267
§ 371 (c)(1),
(2), (4) Date: Apr. 23, 2009

(87) PCT Pub. No.: WO2008/051993
PCT Pub. Date: May 2, 2008

(65) Prior Publication Data
US 2009/0287208 A1 Nov. 19, 2009

Related U.S. Application Data

(60) Provisional application No. 60/853,747, filed on Oct. 24, 2006.

(51) Int. Cl.
*A61B 18/18* (2006.01)
*A61N 1/00* (2006.01)
*A61N 1/30* (2006.01)
(52) U.S. Cl. .............. 606/43; 607/148; 604/20
(58) Field of Classification Search .......... 606/32–36, 606/41–43, 133; 607/115, 148–149, 153; 604/21
See application file for complete search history.

(56) References Cited

U.S. PATENT DOCUMENTS
5,983,131 A 11/1999 Weaver et al.
2007/0179490 A1* 8/2007 Azar et al. .............. 606/28

FOREIGN PATENT DOCUMENTS
WO WO 96/09853 4/1996
WO WO 2006/111968 A2 10/2006

OTHER PUBLICATIONS
International Search Report and Written Opinion of International Application No. PCT/US2007/082267; date of mailing Sep. 30, 2008; 14 pages.

* cited by examiner

*Primary Examiner* — Nicholas D Lucchesi
*Assistant Examiner* — Rebecca E Eisenberg
(74) *Attorney, Agent, or Firm* — Jordan IP Law, LLC; Todd A. Vaughn

(57) ABSTRACT

Disclosed are a method and a device useful for performing cosmetic or medical procedures of an in vivo portion of tissue. The method includes contacting an in vivo portion of tissue with a portion of a pad, substantially saturating the pad with a reactant, contacting the pad with a first electrode so that the first electrode is proximate to the portion of the pad proximate to the in vivo portion of tissue. The method further includes contacting the pad with a second electrode so as to provide an electrical path between the first electrode and the second electrode through the reactant, passing a DC voltage through a circuit including the first electrode, the reactant and the second electrode, thereby forming at least one of: an electrolytic effect, and an electrolytic product of the reactant, proximate to the first electrode.

23 Claims, 21 Drawing Sheets

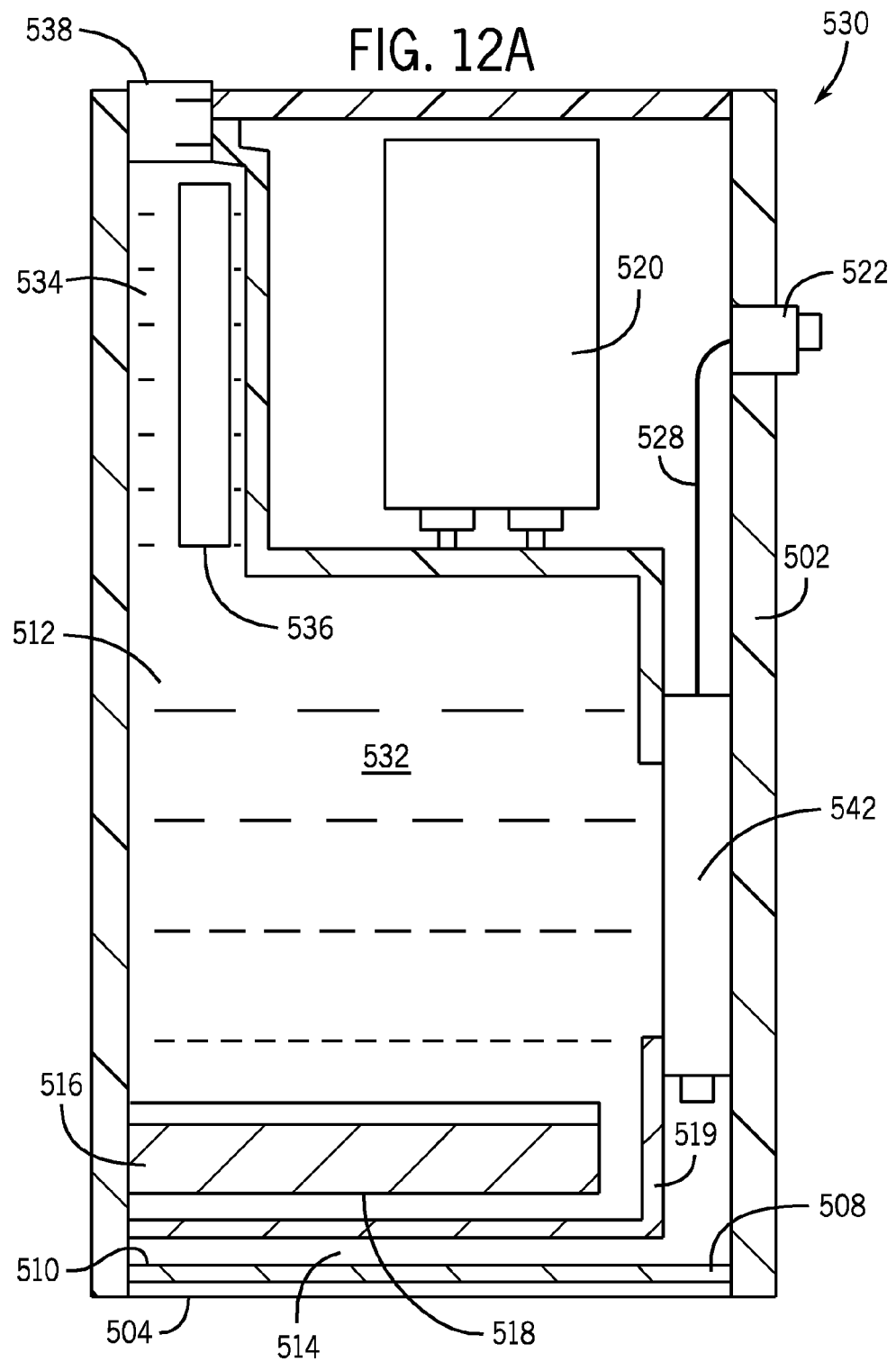
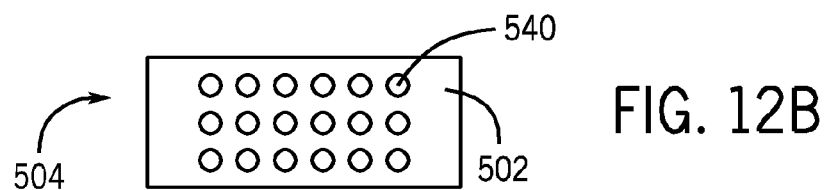

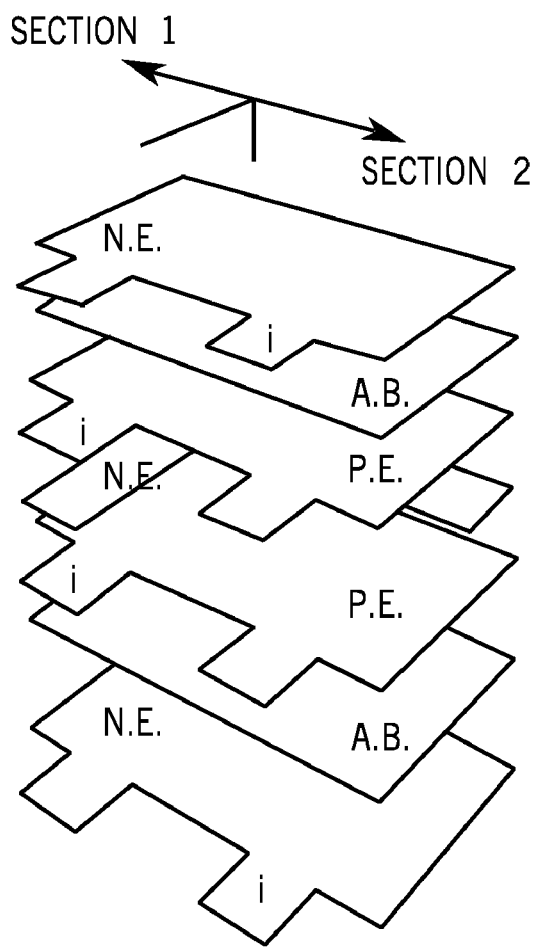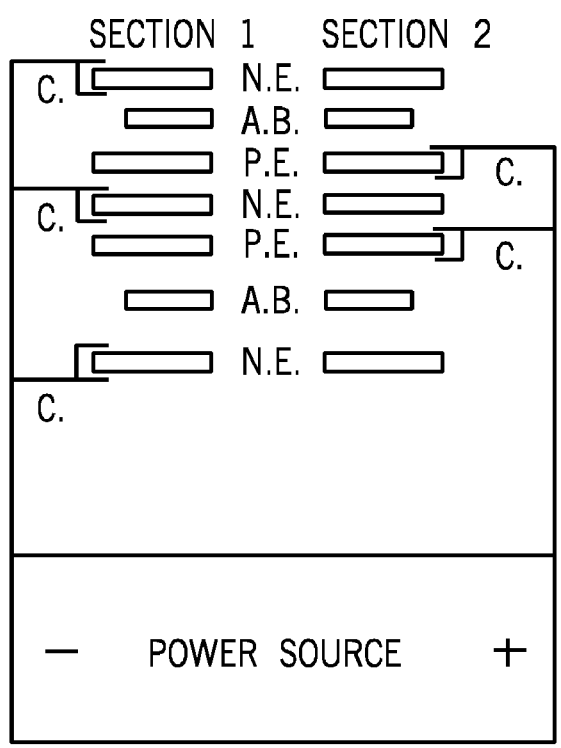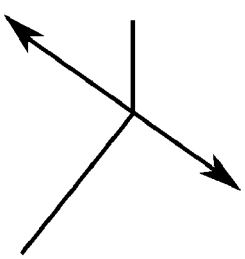
FIG. 15

ELECTROLYTIC TISSUE TREATMENT

CROSS-REFERENCE TO RELATED PATENT APPLICATIONS

This application is the U.S. National Stage of PCT/US2007/082267 having international filing date of Oct. 23, 2007, which claims priority to U.S. Provisional Application 60/853,747, entitled "Electrolytic Tissue Treatment," filed on Oct. 24, 2006, which is incorporated herein by reference in its entirety.

FIELD

The present invention relates to apparatuses and methods for employing electrolysis for cosmetic and therapeutic treatments of tissue.

BACKGROUND

The use of electricity in cosmetology and medicine are well-known: continuous or pulsed low voltage direct current (DC) being used for electrolytic therapy and/or deposition of substances in tissue and AC being used for cutting tissue.

Electrolytic treatments of tissue include, inter alia, use of the following procedures and definitions as used herein:

1. Electrophoresis: the movement of suspended particles through a fluid or gel under the action of an electromotive force applied to electrodes in contact with the suspension.
2. Iontophoresis: the introduction of an ionized substance (such as an active pharmaceutical ingredient) through intact skin by the application of a direct electric current.
3. Electroosmosis: the movement of a liquid out of or through a biological membrane under the influence of an electric field wherein non-charged solutes move along an electro-osmotically induced gradient.
4. Electrolytic desiccation: the removal of water from tissue using an electric current to move an electrolyte desiccant into the tissue.
5. Electokinesis: the motion of particles or liquids that results from or produces a difference of electric potential.
6. Electro-epilation: the use of electrical current to remove hair.
7. Electro-onychomycotomy: the use of electrical current to treat a fungus infection of the nail.

Electrolytic treatments are restricted to using low voltage DC because high voltage DC interferes with nerve and muscle activity, causing pain and tissue damage.

Low voltage DC, though, is an inefficient means of electrolytically affecting tissue, often resulting in deposition of insufficient amounts of a therapeutic substance in the tissue. Alternatively, to achieve sufficient deposition of the substance, low voltage DC requires a lengthy period of time that can be intolerable to a recipient while causing inefficient use of caregiver facilities.

Dispensing electrolytic treatment even using low voltage DC is not completely risk free. For example, low voltage DC electrophoresis that is inadvertently discharged near the heart may cause potentially fatal fibrillation of the ventricles. Additionally, since electrons do not travel in water, reactions at the tissue-electrode interface generally produce oxidation-reduction in substrates that are in contact with the electrodes, often resulting in tissue damage.

In spite of the drawbacks, including the inefficient and lengthy treatments, there are cosmetic treatments that currently use electrolytic DC, for example:

Hyperhydrosis

Primary hyperhydrosis, the overproduction of perspiration, occurs over various body surfaces, including palmar, axillary, plantar, facial, and truncal surfaces. Light to moderate hyperhydrosis is typically treated with applications of 25% aluminum chloride applications several times weekly. Hyperhydrosis that is recalcitrant to topical applications is often treated with iontophoresis.

Electrolytic treatments use devices that supply low DC voltage at 15-18 mA, thereby causing iontophoresis of a solution that typically include aluminum chloride. Treatments last 20-30 minutes each and are provided several times weekly. Resolution of symptoms and patient satisfaction vary considerably: many considering the treatments too time-consuming, inefficient, and/or expensive.

There are two types of sweat glands, eccrine and apocrine. Eccrine sweat glands open to the skin, are under sympathetic cholinergic control, and respond to both thermal and psychological stimulus. Apocrine sweat glands, associated with mammalian sexual scent, are larger than eccrine glands, open to hair follicles, and innervated by sympathetic adrenergic nerve fibers. It is highly likely that eccrine glands respond to different electrical components of iontophoresis than apocrine glands. Not only would a treatment be dispensed more rapidly with a more efficient iontophoretic unit, but also better results could accrue with dual currents: a first for apocrine sweat glands, and a second for eccrine sweat glands.

Potential for Electrolytic Treatments

In addition to iontophoresis for treatment of hyperhydrosis, there are a number of cosmetic treatments that would potentially benefit from a more efficient and efficacious DC electrolytic apparatus.

Electro-Epilation

Referring to FIG. 1, a hair 204 grows from a follicle 208. As follicle 208 is an area where the hair shaft has not fully keratinized, follicle 208 rapidly absorbs electrolytic products.

The life cycle of follicle 208 is divided into 3 phases: anagen, catagen, and telogen. The anagen phase is the phase of active growth. The catagen phase marks regression of follicle 208, and the telogen phase represents a resting period. In the human scalp, the anagen phase lasts approximately 3-4 years. The catagen phase lasts approximately 2-3 weeks, and the telogen phase lasts approximately 3 months.

Onychomycosis

Onychomycosis is an infection that causes fingernails or toenails to thicken, discolor, disfigure, and/or split. Initially disfigurement is primarily a cosmetic concern, though without treatment, the nail can thicken, causing pressure, irritation, and pain in closed shoes.

In diabetics, onychomycosis is both common and dangerous; recent studies have shown a higher rate of amputation in diabetics with onychomycosis compared to those without the infection.

Onychomycosis is difficult to treat because nails grow slowly and receive very little blood supply. Onychomycosis pathogens generally comprise fungal and/or yeast: fungal pathogens including trichophyton rubrum and trichophyton mentagrophytes; and yeast pathogens including candida albicans and candida parapsilosis.

Topical antifungal medication requires 6 months to a year of daily treatments for the nail to regain a healthy, clear, thin appearance. Additionally, there is a relatively high rate of failure and recurrence following treatment.

A well-focused and deep electrolytic intracellular deposition of onychomycotic treatment agents would likely result in fewer treatments and less chance of recurrence.

Actinic Keratosis

Actinic keratosis is a scaly or crusty bump that forms on the skin surface on sun-exposed areas: face, ears, bald scalp, neck, backs of hands and forearms, and lips.

Actinic keratosis can be the first step in the development of skin cancer. It is estimated that up to 10 percent of active lesions, which are redder and tenderer than the rest, will take the next step and progress to squamous cell carcinoma.

The most aggressive form of keratosis, actinic cheilitis, appears on the lips and can evolve into squamous cell carcinoma. Roughly one-fifth of these chelitic-based carcinomas metastasize. More problematic, cancer in the presence of keratosis is not limited to squamous cell carcinoma, but may develop into a highly aggressive and metastatic melanoma.

Treatment is essential in order to avoid the potentially more invasive and extensive treatment of a subsequent malignancy. Current treatments of actinic keratosis include curettage, shave removal, cryosurgery chemical peels and topical creams, for example creams including 5-fluorouracil (5-FU). Each type of treatment is associated with varying initial success but a high rate of return several months to several years down the road.

Actinic keratosis treatment must reach the root of the keratosis in the skin basement membrane to be effective. One theory on why actinic keratosis returns following removal is that the above-noted treatments are not carried down to a sufficient depth due to fear of causing skin scarring. An electrolytic system that deposits medication in and below the basement membrane has greater potential to successfully treat actinic keratosis; without recurrence and without the trauma of ablation or cutting.

Inoperable Tumors

An example of a tumor that is rarely, if ever, surgically excised is a cancerous liver tumor. Surgical excision of liver cancer is not an option because during the surgery, leukemia cells associated with the cancer easily spread to all the organs via the blood stream and the lymph vessels.

There are two main kinds of liver cancer, hepatoma and cholangiocarcinoma. Hepatoma is cancer of the hepatocytes, the main functioning liver cell. Hepatoma is primary liver cancer. Hepatoma usually grows in the liver as a ball-like tumor, invading the normal tissue surrounding it. A history of infection with the hepatitis B virus puts individuals at risk of developing hepatoma.

Cholangiocarcinoma is cancer of the bile duct cells. Cholangiocarcinoma originates in the bile ducts and is often caused by infestation with liver fluke, a parasite called Clonorchis. The cancer grows along the bile ducts in sheets or lines, and is hard to find on X-ray studies.

Most cases of liver cancer are metastases from another organ. Because of its very high blood flow and many biological functions, the liver is one of the most common places for metastases to grow. Tumors that originally arise in the colon, pancreas, stomach, lung, or breast often spread to the liver.

Treatment of liver cancer varies according to the tumor size. Tumors less than 5 cm in diameter are often destroyed using ethanol or acetic acid injected into the tumor.

For tumors greater than 5 cm, a first line treatment for hepatic carcinoma is often chemotherapy where cytotoxic active pharmaceutical ingredients (APIs) are used to destroy cancer cells. APIs are usually given intravenously directly into the hepatic artery during each chemotherapy session. A session typically lasts a few days, followed by recovery period from the side effects. The number of sessions depends on the type of liver cancer and how well it is responding to the APIs.

Chemotherapy APIs often concentrate in fast growing non-liver tissues, causing unpleasant side effects including reduced resistance to infection, nausea, sore mouth and hair loss.

Radiation therapy, often used in conjunction with chemotherapy or lesions above 5 cm, uses X-rays or other high-energy rays to kill cancer cells and shrink tumors. Radiation therapy often adds to chemotherapy side effects.

An electrolytic system that deposits cytotoxic medication with liver tissue has great potential to treat liver cancer, increasing survival rates and reducing side effects.

Electrolytic Alternatives to DC

Recognizing the risk and inefficiency of DC electrolytic treatments to tissue, devices using alternating current (AC) are often used for electrolytic treatment. However, because low frequency AC is accompanied by pain and causes muscle and nerve damage, AC can only be dispensed at higher frequencies.

Medically useful, and safe, high frequency AC has been determined as a current having a frequency of 10,000 or more cycles per second, thereby causing no muscular contractions and having no affect on nerves. In recognition of the damage caused by low frequency AC, regulatory agencies generally limit AC therapeutic modalities to high frequency AC above 10 MHz.

High frequency AC, though, is not useful for electrophoresis procedures because during oscillation, AC constantly changes polarity, causing cell membranes to block electrophoretic movement. The drawbacks of high frequency AC, therefore, limit its use to tissue treatments that require high temperatures. AC, for example, is used to generate heat for cutting tissue, cauterizing bleeding vessels and/or destroying unwanted tissue, including electro-epilation.

U.S. Patent Application published as U.S. 2001023330 teaches a transdermal AC iontophoresis assembly that dispenses pulsed AC frequencies below 100 Hz. However, to limit tissue damage, each pulse duration is less than 2 milliseconds, thereby reducing deposition and increasing treatment time similar to low voltage DC treatments.

U.S. Pat. No. 6,553,253 teaches electrokinetic delivery of therapeutic substances into tissue using AC rectified into DC at a frequency below 1 megahertz. Since this low frequency poses a danger of causing ventricle fibrillation, professional administration is required.

PCT patent application published as WO 2003/103522 teaches injecting a substance into a tissue and providing electrolytic treatments by using the injector as a first electrode in combination with a second remote electrode, similar to mono-polar electrosurgical system.

Articles, included by reference in their entirety, providing background for the present invention, include:

Rosemberg, Y. and Korenstein, R. "Incorporation of macromolecules into cells and vesicles by low electric fields: induction of endocytotic-like process" in Bioelchem. Biophys. Res. Comm. 1997, 42, 275-281

Antov Y, Barbul A, Mantsur H, and Korenstein R. "Electroendocytosis: exposure of cells to pulsed low electric fields enhances adsorption and uptake of macromolecules" in Biophysical Journal 2005, 88(3), 2206-2223.

Entin I, Plotnikov A, Korenstein R, Keisari Y. "Tumor growth retardation, cure, and induction of antitumor immunity in B16 melanoma-bearing mice by low electric field-enhanced chemotherapy" in *Clinical Cancer Research* 2003, 9(8), 3190-3197.

Nordenstrom B E. "Electrochemical treatment of cancer: Variable response to anodic and cathodic fields" American Journal of Clinical Oncology. 1989 December; 12 (6):530-6;

as well as U.S. Pat. Nos. 4,289,135, 4,572,214 and 4,974,595 and China Patent 1042838 to Nordenstrom, et al.

Patents that provide background to the present invention include:

U.S. Pat. No. 6,063,076, "Method and system for removal of hair" using electromagnetic energy to destroy hair matrix;

U.S. Pat. No. 4,155,363 "Electronically controlled apparatus for electrolytic depilation" using electric current that is interrupted between 1 to 3 seconds;

U.S. Pat. No. 5,443,441 "Apparatus and method for transdermal delivery of cosmetic compositions" uses electric current in a range of about. 0.1 mA to about 10 mA;

U.S. Pat. No. 6,039,746 "Patch electrolysis system and method for removing hair from skin" applies an electrolysis current through patches secured to a skin surface;

European Patent EP 0824003 "Hair removal device and method" relies on iontophoretic deposition of thioglycolate depilatories;

PCT publication WO 2001/87171 "Method and System for Removal of Hair with a Conductive Layer" uses electromagnetic energy to destroy hair matrix;

European Patent EP 0783347 "Method of Hair Removal" by removing the hair and treating the exposed follicle to inhibit hair regeneration; and Despite the need for effective electrolytic treatments of tissue, there is no apparatus that provides electrolytic tissue treatment devoid of the above limitations.

SUMMARY

Embodiments of the present invention successfully address at least some of the shortcomings of the prior art by providing methods and apparatuses using electrolysis for the generation of ions for cosmetic and therapeutic treatments of tissue, including topical treatments.

According to an aspect of the invention, electrolytic tissue apparatus and treatment methods are provided; wherein the apparatus comprises an Electrolytic Conversion Device (ECD) including a reactant, at least a portion of the reactant being electrolysable. The ECD further includes a pad substantially soaked with the reactant, the pad having a lower pad surface, a first electrically insulating layer having an upper insulation surface substantially in contact with the lower pad surface and a first opening passing through the insulating layer. In addition, the ECD includes two terminals comprising first and second terminals configured for connecting to a DC power source, at least two electrodes substantially contacting the pad and spaced a distance from each other, such that a first electrode connected to the first terminal contacts the pad substantially proximate to the first opening, and a second electrode connected to the second terminal contacts the pad substantially distant from the first opening.

In exemplary embodiments, the apparatus further comprises a DC power source connected to the two terminals so that the first electrode is an anode. Optionally, the DC power source is connected to the terminals so that the first electrode is a cathode.

In a further exemplary embodiment, the pad proximate to the first opening is compliant; comprising a material selected from the group consisting of woven cloth, non-woven cloth, fabric, fibers, spongy material, rubber, cotton, wool, polyester and polyamide.

Optionally, the first opening has a shape selected from the group consisting of square, oval, circular, round, rectangular, curved, triangular, circular section and arced.

In an additional exemplary embodiment, at least a portion of the reactant is a solution and reactant includes at least one of an API and a salt. Optionally, the reactant comprises at least one of the group consisting of an anti-mitotic agent, a photoreactive agent, an enzyme, an atomic particle-emitting substance, an antigenically tagged API a cell receptor tagged API and a genetically tagged API. In an alternative exemplary embodiment, the reactant comprises at least one of the group consisting of a desiccator, an epilator, an anti-fungal agent, and a catalyst.

In some exemplary embodiments, a product of electrolysis of the reactant comprises at least one of the group consisting of an anti-mitotic agent, a photoreactive agent, an enzyme, an atomic particle-emitting substance, an antigenically tagged API, a cell receptor tagged API and a genetically tagged API. Alternatively, a product of electrolysis of the reactant comprises at least one of the group consisting of desiccator, epilator, anti-fungal agent, and a catalyst. In some embodiments, at least a portion of the reactant is susceptible to at least one of the group consisting of electrophoresis, iontophoresis, electroosmosis, and electokinesis.

In exemplary embodiments, at least a portion of the first electrically insulating layer is of a material comprising a material having a property selected from the group consisting of compliant, flexible, plastic, and rigid. Optionally, at least a portion of the first electrically insulating layer is impermeable to the passage of gas.

In alternative exemplary embodiments, at least a portion of the first electrically insulating layer is of a material comprising a material from the group consisting of foil, film, sheet, membrane, non-woven cloth, and woven cloth. Optionally, the first insulating material is selected from the group consisting of paper, polyester, polyethylene, polypropylene and silicone. Additionally the first insulating layer has a thickness of less than about 5 μm. Alternatively, the first insulating layer has a thickness of less than about 100 μm. In still other embodiments, the first insulating layer has a thickness of more than about 5 μm. In yet other embodiments, the first insulating layer has a thickness of more than about 100 μm.

Optionally, the insulating material is cuttable.

In further exemplary embodiments, the first insulating layer includes a lower surface substantially in contact with a first base layer, the first base layer having a first opening substantially aligned with the insulation layer first opening.

Optionally, the first base layer has a thickness of less than about 15 μm. Alternatively, the first base layer has a thickness of less than about 100 μm. In still alternative embodiments, the first base layer has a thickness of no more than about 15 μm; or additionally, the first base layer has a thickness of no more than about 100 μm.

In exemplary embodiments, at least a portion of the first base layer is selected from the group consisting of aluminum, stainless steel, noble metal, and plastic.

In some exemplary embodiments, a second electrically insulating layer is included wherein the at least two electrodes and the pad are contained between the first electrically insulating layer and second electrically insulating layer.

Optionally, the second electrically insulating layer is substantially contiguous with the first electrically insulating layer, thereby together substantially containing the pad and the at least two electrodes.

In some embodiments, a second base layer substantially covers the second insulating layer. Further, at least a portion of the second base layer is selected from the group consisting of aluminum, stainless steel, noble metal, and plastic. Optionally the second base layer is substantially contiguous with the first base layer, thereby substantially electrically sealing at least a portion the first and second insulating layers.

In an exemplary embodiment, the apparatus further comprises a DC power source connected to the terminals; the DC power source provides at least about 1 volt. Alternatively, the DC power source provides at least about 2 volts; even at least about 4 volts; or even at least about 6 volts.

In alternative embodiments, the DC power source provides no more than about 40 volts; or the DC power source provides no more than about 60 volts. Optionally the DC power source provides no more than about 80 volts; or the DC power source provides no more than about 100 volts.

In some additional exemplary embodiments, the DC source is configured to provide a current of at least about 0.1 mA; or the DC source is configured to provide a current of at least about 2 mA. Alternatively the DC source is configured to provide a current of at least about 3 mA; or the DC source is configured to provide a current of at least about 4 mA. Further, the DC source is configured to provide a current of no more than about 100 mA; or the DC source is configured to provide a current of no more than about 250 mA. In still other embodiments the DC source is configured to provide a current of no more than about 500 mA; or the DC source is configured to provide a current of no more than about 1000 mA.

In an exemplary embodiment, the DC source is configured to provide a continuous current. Alternatively, the DC source is configured to provide a pulsed current and the current has a pulse width of at least about $1 \times 10^{-5}$ seconds. In other embodiments the current has a pulse width of at least about $3 \times 10^{-9}$ seconds. In still other embodiments, the current has a pulse width of no more than about 0.1 second. In still other embodiments, the current has a pulse width of no more than about 0.01 second. And in other embodiments, the current has a pulse width of no more than about $1 \times 10^{-5}$ seconds. Further, in other embodiments, the current has a pulse width of no more than about $3 \times 10^{-9}$ seconds.

In some exemplary embodiments the upper insulation layer, the pad, and the lower insulation layer constitute a substantially planar laminated construct. Optionally, the substantially planar laminated construct is substantially flexible.

In additional exemplary embodiments the first insulating layer comprises at least two angulated walls defining an internal volume there between, wherein the first electrode, the second electrode and the pad are contained within the volume. Optionally, the at least two angulated walls substantially form a needle-like configuration. Optionally, the needle-like configuration is configured to pierce tissue. Further, optionally, the apparatus is substantially implantable in vivo.

In some embodiments, the apparatus is substantially implantable in a tissue selected from the group consisting of soft tissue, bone, cartilage and liquid.

In other exemplary embodiments, the DC is provided by at least one of an AC to DC converter and a battery.

Optionally, the DC source is configured to provide a potential of at least about 1 volt. Alternatively, the DC source is configured to provide a potential of at least about 2 volts; or the DC source is configured to provide a potential of no more than about 100 volts. In still other embodiments, the DC source is configured to provide a potential of no more than about 1000 volts.

Further, in some embodiments, the DC source is configured to provide a continuous current.

In further exemplary embodiments, the apparatus includes an oscillator connected to the provided DC, the oscillator producing a pulse width of at least about $1 \times 10^{-5}$ seconds. In other embodiments the current has a pulse width of at least about $3 \times 10^{-9}$ seconds. In still other embodiments, the current has a pulse width of no more than about 0.1 second.

In still other embodiments, the current has a pulse width of no more than about 0.01 second. And in other embodiments, the current has a pulse width of no more than about $1 \times 10^{-5}$ seconds. Further, in other embodiments, the current has a pulse width of no more than about $3 \times 10^{-9}$ seconds.

In some exemplary embodiments, the apparatus includes at least one signal amplifier adapted to receive and amplify the at least one monopolar pulse. Further, the at least one signal amplifier is adapted to provide a first polarity to the first terminal, and a second polarity to the second terminal.

Optionally, the at least one signal amplifier comprises at least one of a resistor, a capacitor, and a transistor.

In some embodiments, the DC source is configured to provide a current of at least about 0.1 mA; or the DC source is configured to provide a current of at least about 2 mA. Alternatively, the DC source is configured to provide a current of at least about 3 mA or the DC source is configured to provide a current of at least about 4 mA.

In alternative exemplary embodiments the DC source is configured to provide a current of no more than about 100 mA; or the DC source is configured to provide a current of no more than about 250 mA. Alternatively, the DC source is configured to provide a current of no more than about 500 mA; or the DC source is configured to provide a current of no more than about 1000 mA.

In some exemplary embodiments, at least a portion of the first base layer is electrically conductive. Further, in alternative embodiments, the apparatus includes a side electrode in electrical contact with the electrically conductive portion of the first base layer. Optionally the side electrode is configured to produce an alternating electrical field.

In some embodiments, the side electrode includes at least one inverter.

In other exemplary embodiments, the apparatus comprises at least four electrodes, including a third electrode and a fourth electrode in contact with the pad so that the third electrode is electrically connected to the fourth electrode through the reactant.

Optionally, the apparatus further comprises at least two openings, a first opening and a second opening, wherein the second opening is proximate to the third electrode.

According to the teachings of the present invention, there is also provided a device useful for cosmetic and/or therapeutic treatment of a surface (such as the skin) presumably by the generation of electrolysis products in proximity of the surface, comprising: a) a reservoir configured to hold an electrolytic fluid; b) a conduit configured to transport an electrolytic fluid from the reservoir to emerge out at a contact surface; c) a first electrode having an electrode face functionally associated with the conduit (that is positioned so as to make electrical contact with an electrolytic fluid present in the conduit) in proximity of the contact surface; d) a second electrode having an electrode face functionally associated with the conduit (that is positioned so as to make electrical contact with an electrolytic fluid present in the conduit) spaced a distance from the first electrode and not closer to the contact surface than the first electrode; and e) a power inlet, to direct DC electrical power to the first electrode and the second electrode.

In embodiments, interposed between the first electrode and the second electrode is a component that prevents or reduces flow of electrolytic fluid between the electrodes, but allows the movement of ions therebetween. In embodiments, such a component includes agar agar or a material that allows the passage of ions therethrough (e.g., membranes and separators known in the art of battery making, for example, UltraLith™ from Advanced Membrane Systems, North Billerica, Mass., USA. In such a way, when electrolytic fluid flows out of the device from the reservoir through the conduit and out at the contact surface, ions are not physically carried from the second electrode to the first electrode.

In embodiments, the power inlet is configured to receive DC power from a power supply. In embodiments, the power inlet is configured to convert AC electricity received from a power supply to DC electrical power, for example by integrating an AC to DC converter.

In embodiments, the reservoir comprises a void.

In embodiments, the reservoir comprises an absorbent material, similar to the pad of embodiments described above, for example of a woven cloth, a nonwoven cloth such as a felt, fabric, a fibrous material or a spongy material.

In embodiments, the conduit is a capillary conduit. In embodiments, the conduit comprises a capillary passage (analogous to a fountain pen or the like). In embodiments, the conduit comprises a tangible material configured for capillary transport of the electrolytic fluid (similar to the pad of embodiments described above, for example of a woven cloth, a nonwoven cloth such as a felt, fabric, a fibrous material or a spongy material) that wicks the fluid.

In embodiments, a dimension of the conduit when emerging at the contact surface is no more than about 200 micrometers and even no more than about 100 micrometers. In embodiments, the conduit emerges at the contact surface as a slit that is no more than about 200 micrometers wide, in embodiments between 2 and 6 cm long. In embodiments, the conduit emerges at the contact surface as one or more perforations or holes, each such hole having a diameter of no more than about 200 micrometers or even no more than about 100 micrometers.

In embodiments, the conduit comprises a void and the face of the first electrode is inside the void. In embodiments, the conduit comprises a void and the face of the first electrode comprises a portion of a wall of the void. In embodiments, the conduit comprises a tangible material and the face of the first electrode contacts the tangible material.

In embodiments, the conduit comprises a void and the face of the second electrode is inside the void. In embodiments, the conduit comprises a void and the face of the second electrode comprises a portion of a wall of the void. In embodiments, the conduit comprises a tangible material and the face of the second electrode contacts the tangible material.

In general, it is at the first electrode that the electrolysis products are formed. Since the greater the concentration of the electrolysis products, the greater the efficacy of the device, it is preferred that the face of the first electrode be relatively sharp and to be as close as possible to the treated surface so as so as to have an effect in as small a volume of electrolytic fluid as possible.

In embodiments, the face of the first electrode is at a distance of no greater than 2 mm, no greater than 1 mm, no greater than 0.5 mm and even no greater than 0.4 mm from the contact surface. In embodiments, the face of the first electrode substantially comprises a portion of the contact surface.

In embodiments, the face of the first electrode is substantially planar.

In embodiments, the face of the first electrode encircles a portion of the conduit.

In embodiments, the face of the first electrode has a width dimension substantially similar in size to a width dimension of the conduit at the contact surface.

In embodiments, the face of the first electrode has a width dimension of at least about 2 cm, at least about 2.5 cm and even at least about 3 cm. In embodiments, the face of the first electrode has a width dimension of no more than about 10 cm, no more than about 6 cm and even no more than about 4 cm.

In embodiments, the face of the first electrode has a breadth dimension of no more than about 2 mm, no more than about 0.5 mm, no more than about 0.3 mm and even no more than about 0.1 mm.

In embodiments, the face of the first electrode has a breadth dimension substantially in the flow direction of fluid through the conduit proximate to the contact surface.

In embodiments, the face of the first electrode has an area of no more than about 200 mm$^2$. In embodiments, the face of the first electrode has an area of no more than about 100 mm$^2$ (e.g., about 2.5 mm by 40 mm).

Generally there are fewer limitations as to the dimensions and construction of the second electrode. In general, it is desirable that the second electrode be close to the first electrode in order to reduce resistance, but far from the first electrode to reduce the rate of recombination of electrolysis products. In embodiments, the face of the second electrode is at least about 1 mm, at least about 1.5 mm and even at least about 2.5 mm from the face of the first electrode. In embodiments, the face of the second electrode is no more than about 20 mm, no more than about 10 mm and even no more than about 5 mm from the face of the first electrode. Generally a distance of between 2.5 mm and 5 mm is believed to provide reasonable results.

In embodiments, the face of the second electrode is more distant from the contact surface than the face of the first electrode.

In embodiments, the area of the face of the second electrode is substantially greater than the area of the face of the first electrode. In embodiments, the area of the face of the second electrode is at least two times greater than the area of the face of the first electrode, and even at least four times greater than the area of the face of the first electrode. In principle it is desirable that the second electrode have a large surface area as possible so that the size of the second electrode is not a current-limiting factor.

In embodiments, the device further comprises a power supply configured to provide electrical power to the power inlet. In embodiments, the power supply is an AC power supply. In embodiments the power supply is a DC power supply. In embodiments, the power supply is configured to provide power having characteristics as described above. In embodiments, the power supply is configured to provide electrical power having a potential of at least 1, at least 1.5V, at least 4.5V, at least 6V and even at least 9V. Further, it has been found that potentials greater than about 9 V may lead to an increase in temperature of the electrolytic solution, wasting energy and causing user discomfort. Preferably, the electrical power supply is configured to provide electrical power having a potential between about 1 V and about 9 V, corresponding to standard batteries. In embodiments, the power supply is configured to provide at least about 0.1 mA per mm$^2$ of the face of the first electrode, (approximately 10 mA on a 2.5 mm by 35 mm electrode face). In embodiments, the power supply is configured to provide at least about 0.2 mA per mm$^2$ of the face of the first electrode, (approximately 20 mA on a 2.5 mm by 35 mm electrode face). In embodiments, the power supply is configured to provide between about 1 mA and 3 mA per mm$^2$ of the face of the first electrode (approximately 100 and 300 mA and even more on a 2.5 mm by 35 mm electrode face).

In embodiments, the device further comprising a portable housing bearing the reservoir, the conduit, the first electrode, the second electrode and the power inlet. In embodiments, some or all of the components are contained within the portable housing. In embodiments, some of the components, (e.g., the first electrode) are at least in part apparent on the outside of the portable housing. In embodiments, the contact surface is positioned at an end of the portable housing. In embodiments, the portable housing further comprises at least one holding surface distinct from the contact surface. In embodiments, the portable housing is elongated with the contact surface positioned at one end with the holding surface substantially longer (generally being at least 5 cm but less than 15 cm long for convenient holding) than the contact surface. In the embodiments, the holding surface is rounded.

In embodiments, the portable housing further bears (and even contains) a power supply (e.g., a battery, a rechargeable battery).

In embodiments, the device further comprises a port in fluid communication with the reservoir configured for charging the reservoir with an electrolytic fluid.

In embodiments, the device further comprises an electrolytic fluid in the reservoir. In embodiments, the electrolytic fluid is an aqueous salt solution. In embodiments, the electrolytic fluid is an aqueous NaCl solution. In embodiments, the NaCl solution is at least about 50% of saturated. In embodiments, the NaCl solution is at least about 80% of saturated. In embodiments, the NaCl solution is a substantially saturated solution.

In embodiments, the first electrode is a cathode and the second electrode is an anode. In embodiments, the first electrode is an anode and the second electrode is a cathode.

According to the teachings of the present invention, there is also provided a method for topical (therapeutic or cosmetic) treatment of skin comprising: a) positioning a face of a first electrode proximate to the skin; b) positioning a face of a second electrode so that an electrical path between the face of the first electrode and the face of the second electrode does not pass through the body; c) bringing the face of the first electrode and the face of the second electrode in electrical contact through an electrolytic fluid; and d) passing a current through the face of the first electrode, the electrolytic fluid and the face of the second electrode so as to generate products of electrolysis of components of the electrolytic fluid in the proximity of the face of the first electrode, the products useful in achieving a desired effect, whereby at least one desired electrolytic effect is produced, as discussed herein, for example the electrolysis products contact the skin to have the desired effect, or the electrolysis products produce a gradient that leads to the desired effect.

In embodiments, the face of the first electrode is positioned no more than about 2 mm, no more than about 1 mm and even no more than about 0.5 mm from the skin. In embodiments, the face of the first electrode is positioned so as to substantially contact the skin (e.g., through a thin layer of electrolytic fluid).

In embodiments, the current has characteristics as described above.

In embodiments, the current is at least about 0.1 mA per $mm^2$ of the face of the first electrode (corresponding to 10 mA on a 2.5 mm by 35 mm electrode face).

In embodiments, the current is at least about 0.2 mA per $mm^2$ of the face of the first electrode (corresponding to 20 mA on a 2.5 mm by 35 mm electrode face).

In embodiments, the current is between about 1 mA and 3 mA per $mm^2$ of the face of the first electrode (corresponding to 100-300 mA on a 2.5 mm by 35 mm electrode face).

In embodiments, the desired effect is a cosmetic effect.

In embodiments, the cosmetic effect is hair removal. For example, to effect hair removal in accordance with the teachings of the present invention, a saturated NaCl electrolytic fluid is used where the first electrode is an anode and the second electrode is a cathode.

In embodiments, the cosmetic effect is pore cleansing.

In embodiments, the desired effect is a therapeutic effect.

According to an aspect of the invention, a method is provided for treating of an in vivo portion of the tissue. The method comprises contacting an in vivo tissue portion with a portion of a pad, substantially saturating the pad with a reactant. The method additionally comprising, contacting the pad with a first electrode so that the first electrode is proximate to the portion of the pad proximate to the area of tissue; contacting the pad with a second electrode so as to provide an electrical path between the first electrode and the second electrode through the reactant. The method furthermore comprising, passing a DC through a circuit including the first electrode, the reactant and the second electrode, thereby forming at least one of an electrolytic effect, and an electrolytic product of the reactant, proximate to the first electrode.

In some exemplary embodiments, the second electrode is electrically distanced from the area of tissue so as to substantially prevent passage of current through the tissue.

In other exemplary embodiments, the electrical distancing includes interposing an electrical insulator between the pad and the in vivo tissue portion in proximity of the second electrode.

In some embodiments, a voltage of the passing current provides at least about 1 volt. Alternatively, a voltage of the passing current provides at least about 2 volts; even at least about 4 volts; or even at least about 6 volts.

In alternative embodiments, a voltage of the passing current provides no more than about 40 volts; or the voltage of the passing current provides no more than about 60 volts. Optionally the voltage of the passing current provides no more than about 80 volts; or the DC power source provides no more than about 100 volts.

In some additional exemplary embodiments, a DC source is configured to provide a current of at least about 0.1 mA; or the DC source is configured to provide a current of at least about 2 mA. Alternatively the DC source is configured to provide a current of at least about 3 mA; or the DC source is configured to provide a current of at least about 4 mA. Further, the DC source is configured to provide a current of no more than about 100 mA; or the DC source is configured to provide a current of no more than about 250 mA. In still other embodiments the DC source is configured to provide a current of no more than about 500 mA; or the DC source is configured to provide a current of no more than about 1000 mA.

In some embodiments, a DC source is included that is configured to provide a continuous current.

In alternative embodiments, a DC source is configured to provide a pulsed current; and the current has a pulse width of at least about $1 \times 10^{-5}$ seconds. In other embodiments the current has a pulse width of at least about $3 \times 10^{-9}$ seconds. In still other embodiments, the current has a pulse width of no more than about 0.1 second. In still other embodiments, the current has a pulse width of no more than about 0.01 second. In other embodiments, the current has a pulse width of no more than about $1 \times 10^{-5}$ seconds. Further, in other embodiments, the current has a pulse width of no more than about $3 \times 10^{-9}$ seconds.

Optionally, while passing the DC, the electrolytic product migrates to form a chemoelectric gradient proximate to the first electrode along a surface of the tissue, and a first distance below the surface of the tissue.

In an exemplary embodiment, the distance the electrolytic product migrates below the surface increases with time.

In an exemplary embodiment, the method device includes a first opening having a cross sectional area and as the migration increases, the product forms a cross sectional area below the surface that is related to the first opening cross sectional area.

In some exemplary embodiments, the reactant comprises an API. Optionally, the API is selected from the group of APIs consisting of antimycotic, anti-cancer, hair removal, pre-cancerous treatment and hyperhydrotic treatment APIs. In some embodiments, the antimycotic API is selected from the group consisting of miconazole, clotrimazole, econazole, ketoconazole, ciclopirox, naftifine, and terbinafine.

In other embodiments, the anti-cancer API is selected from the group consisting of anti-mitotic, photoreactive, atomic particle-emitting, antigenically tagged, and genetically altering APIs.

In an alternative embodiment, the hair removal API is selected from the group consisting of Thioglycolate depilatories, Eflornithine and Hydroxyl ion producing reactants.

Optionally, the anti pre-cancerous API is selected from the group consisting of Jessners solution, trichloroacetic acid, bleomycin, hydroxyurea and 5-fluorouracil (5-FU).

In still some other embodiments, the reactant comprises a reactant selected from the group consisting of hyperhydrotic treating substances, including aluminum chloride API.

In other embodiments the cancer is electrolytically treated with an anti-cancer API.

In some embodiments, the tissue includes excess hair and the reactant includes at least one hair removal API.

Optionally, the tissue contains one mycotic nail fold and the reactant includes at least one antimycotic API. Alternatively, the tissue contains at least one cancer cell and the reactant includes at least one anti-cancer API.

In some further embodiments, the tissue contains at least one hyperhydrotic gland and the reactant includes at least one hyperhydrotic treating substance.

In some optional embodiments, the tissue contains at least one cell exhibiting actinic keratosis and the reactant includes at least one precancerous treating substance.

In some further embodiments, the method includes applying an AC potential to the tissue, thereby enhancing the electrolytic effect.

In some additional embodiments, the method includes providing a side electrode in contact with the tissue, applying an alternating current to the side electrode, thus increasing a rate at which the product migrates.

In some further additional embodiments, the method further includes contacting the pad with a third electrode and a fourth electrode, interposing an insulating layer between the tissue and the pad proximate to the third electrode, passing current through the third and fourth electrodes with a DC of at least about 1 mA, and migrating the first electrolytic product into a surface of the tissue proximate to the fourth electrode.

Optionally, the first and third electrodes have a first polarity and the second and fourth electrodes have an opposite polarity.

In some embodiments, a second electrolytic reactant is included wherein the first reactant reacts to a first polarity and the second reactant reacts to an opposite polarity.

According to an aspect of the invention, a method is provided for cosmetically improving an area of unaesthetic skin using an electrolytic treatment, comprising; contacting an area of unaesthetic skin with a pad, contacting the pad with a first electrode and a second electrode, interposing an insulating layer between the skin and the second electrode, and passing a DC of at least about 1 mA between the first and second electrodes, thereby cosmetically improving the area.

In some embodiments, skin is selected from the group consisting of at least one of hirsute skin, onychomycotic skin, hyperhydrotic skin, and actinic keratosis-affected skin.

Optionally, the method further includes providing a side electrode in contact with the skin, applying an alternating current to the side electrode thereby. In a further exemplary embodiment, the method further includes contacting the skin with a third electrode and a fourth electrode, passing current through the third and fourth electrodes with a DC and increasing at least one of, a rate at which the skin cosmetically improves, and an area in which the skin cosmetically improves.

According to an aspect of the invention, electrically powered devices and methods of using such devices for the treatment of tissue, particularly the skin of a subject, are provided. Similar to the other apparatuses and methods previously described, the electrically powered devices are useful for cosmetic and/or therapeutic tissue treatments. For example, the devices may be used for epilation and any of a number of the skin conditions described above. An electrically powered device is described for the treatment of a subject's skin, and in some embodiments, the treatment comprises epilation.

In one embodiment, an electrically powered device for the treatment of a subject's skin is provided. The device includes a first negative electrode, a first positive electrode, a conduit and a first reservoir for holding a fluid. The conduit is positioned intermediate the first negative electrode and the first positive electrode. In embodiments, a first portion of the conduit is in contact with the first positive electrode and a second portion of the conduit is in contact with the first negative electrode. In some embodiments, the first and second conduit portions are distant from each other. In embodiments, the conduit is sandwiched between the first positive and first negative electrode.

In embodiments, the first negative electrode, the first positive electrode and the conduit are in communication with the fluid. In embodiments, an electrolytic fluid is provided. In embodiments, the electrolytic fluid provides conditions, such that when the electrodes are connected to a power source, electrochemical reactions can take place in the electrolytic fluid, yielding electrolytic products. In embodiments, the electrochemical reactions take place when current is supplied. In embodiments, the current is a high current. In embodiments, the conduit is formed of a material that when in contact with the fluid, provides an environment such that when the electrodes are connected to a power source, electrochemical reactions take place. In embodiments, the conduit is formed of a material that provides an electrolytic fluid when in contact with the fluid. For example, in embodiments, the conduit comprises salt, the fluid comprises water, and when the water contacts the conduit, an electrolytic solution comprising salt water is formed.

In embodiments, contacting the conduit with the fluid provides a conductive conduit. In embodiments, the conduit comprises an ion bridge. In embodiments, the conduit completes a circuit (e.g., an electrochemical system) and allows electrochemical reactions to take place in the electrolytic fluid. In embodiments, the electrochemical reactions occur in the presence of high current.

In embodiments, the first negative electrode and the first positive electrode are configured to allow current to pass between them. In embodiments, electrolytic products are formed when electrical power is provided to the electrolytic fluid. In embodiments, the first reservoir is configured to release the electrolytic products to the subject's skin. In embodiment, the electrolytic products comprise hydroxide ions. In embodiments, the pH of the electrolytic products is from about 10 to about 14.

In embodiments, the first positive electrode and the first negative electrode are formed as plates, and the conduit is substantially planar. In embodiments, the first positive electrode and the first negative electrode and the conduit are stacked to form a substantially laminate construct.

In embodiments, the conduit may be a salt bridge. In embodiments, the conduit comprises a support, a substrate and a salt. For example, in embodiments, the salt includes one or more of NaCl (sodium chloride), KCl (potassium chloride), LiCl (lithium chloride), $Na_2HPO_4$ (dibasic sodium phosphate), $CaCl_2$ (calcium chloride), the substrate includes one or more of agarose, agar, polyacrylate, gelatin, alginate-Ca, and the support includes one or more of paper, fabrics, non-woven materials, cotton, plastic tubing and mesh. In embodiments comprising more than one conduit, the conduits may be the same or different.

In embodiments, the device includes a housing configured to contain the first positive electrode, the first negative electrode, the conduit and the first reservoir. In embodiments, the housing includes a contact surface. Generally, the contact surface includes at least one aperture configured to allow fluid and electrolytic products to flow therethrough. In embodiments, the first negative electrode is positioned proximate to the aperture or apertures of the housing contact surface.

In embodiments, the electrically powered device for the treatment of a subject's skin includes multiple negative and multiple positive electrodes. In embodiments, a second negative electrode and a third negative electrode are provided. In embodiments, the second and third negative electrodes are formed as plates. In embodiments, the second negative electrode is conductive on both sides and the third negative electrode has a conductive side and a non-conductive side, and the first negative electrode has a conductive side and a non-conductive side. In embodiments, the first, second and third negative electrodes are in communication with the fluid. In embodiments including a housing, a first portion of the first negative electrode, second negative electrode and third negative electrode are positioned proximate to the contact surface aperture or apertures of the housing.

In embodiments, the device includes a second positive electrode formed as a plate and having a conductive side and a non-conductive side. In embodiments, the first positive electrode also has a conductive side and a non-conductive side. In embodiments, the device includes a second conduit. In embodiments, the electrodes and the first and second conduit form a substantially laminate construct configured to produce hydroxide ions in the first reservoir when electrical current flows between the electrodes and when electrolytic fluid is present.

In embodiments, the fluid comprises water, surfactant, API, a compound whose electrolytic product comprises an API, or a combination thereof. In embodiments, the surfactant forms bubbles in the first reservoir when current flows between the electrodes. In embodiments including a housing, the electrolytic products (e.g., hydroxide ions) exit the first reservoir through the contact surface apertures with the bubbles.

In embodiments, the device includes a handle. In embodiments, the handle is operably secured to the housing.

In embodiments, the device includes additional reservoirs (e.g., a second reservoir) configured to hold compounds such as a surfactant, an API or a compound whose electrolytic product comprises an API. Exemplary compounds (e.g., APIs) have been described previously and will not be repeated here.

In embodiments, the housing contact surface contacts the skin. In embodiment, the housing contact surface is proximate to the skin.

In embodiments, one or more of the negative electrodes is proximate to the skin. In embodiments, one or more of the negative electrodes contacts the skin. In embodiments, one or more of the negative electrodes contacts hair.

In other embodiments, one or more of the positive electrodes is proximate to the skin. In embodiments, one or more of the positive electrodes contacts the skin. In embodiments, one or more of the positive electrodes contacts the hair.

In embodiments, one or more of the electrodes is positioned proximate to the skin. In embodiments, one or more of the electrodes contacts the skin. In embodiments, one or more of the electrodes contacts the hair.

In embodiments, the device includes a razor. In embodiments, the razor is operably secured to the housing. In embodiments, the device includes one or more razor blades. In embodiments, the one or more razor blades are positioned to shave substantially simultaneously with epilation (e.g., damaging the cells responsible for hair growth). In embodiments, one or more of the electrodes comprises a razor blade. In embodiments, one or more of a first, second or third negative electrodes comprises a razor blade. In embodiments, one or more of a first or second positive electrode comprises a razor blade. In embodiments, one or more of a positive electrode and one or more of a negative electrode comprise a razor blade.

In embodiments, methods for treatment of a subject's skin are also provided. In embodiments, the treatment comprises epilation. In embodiments, methods include providing a first negative electrode, a first positive electrode, a conduit and an electrolytic fluid. In embodiments, a portion of the first negative electrode is positioned proximate to skin. In embodiments, the conduit is positioned intermediate to the first positive electrode and the first negative electrode. In embodiments, the first negative electrode, the first positive electrode and the conduit are contacted with a fluid. In embodiments, an electrolytic fluid is provided. In embodiments, an electrical current is provided to flow between the first positive electrode and the first negative electrode, through the electrolytic fluid. In embodiments, contacting the conduit with the fluid provides the electrolytic fluid.

In embodiments, contacting the conduit with the fluid provides an electrically conductive conduit. In embodiments, the conduit comprises an ion bridge. In embodiments, the conduit completes a circuit (e.g., an electrochemical system). In embodiments, contacting the conduit with fluid provides electrolytic fluid. In embodiments, electrochemical reactions take place in the electrolytic fluid. In embodiments, the electrochemical reactions occur in the presence of high current. In embodiments, electrolytic products are formed from the electrochemical reactions in the electrolytic fluid. In embodiments, the electrolytic products are formed proximate to the portion of the first negative electrode positioned proximate to the subject's kin. In embodiments, the electrolytic products are released to the subject's skin.

In embodiments, the fluid includes water, and the conduit is a salt bridge. In embodiments, the salt bridge includes agarose and sodium chloride and the electrolytic fluid includes salt water. In embodiments, the electrolytic products comprise hydroxide ions. In embodiments, the pH of the electrolytic products is from about 10 to about 14.

In embodiments, releasing electrolytic products include combining a surfactant with the electrolytic fluid such that bubbles form when the electrical current is provided. In embodiments the electrolytic products are released to the skin with the bubbles. In embodiments, the pH of the electrolytic products is from about 10 to about 14.

In embodiments, the methods further include providing a second negative electrode, a third negative electrode, a second positive electrode and a second conduit, wherein a portion of the second negative electrode and a portion of the third negative electrode are positioned proximate to the skin. In embodiments, the electrodes and conduits are assembled into a substantially laminate structure and configured to produce electrolytic products proximate to the portions of the first, second, and third negative electrodes that are proximate to the skin when current flows between the electrodes. In embodiments, the fluid is water, and the second conduit comprises agarose and sodium chloride. In embodiments, the electrolytic products comprise hydroxide ions. In embodiments, releasing electrolytic products include combining a surfactant with the electrolytic fluid such that bubbles form when the electrical current is provided. In embodiments, the bubbles are released to the skin. In embodiments, the electrolytic products are released to the skin with the bubbles.

In embodiments, a razor or razor blade is provided. In embodiments, shaving is performed substantially simultaneously with the release of the electrolytic products to the skin. In embodiments, epilation occurs substantially simultaneously with shaving. In embodiments, the razor is operably secured to the housing.

Thus, embodiments of the present invention successfully address at least some of the shortcomings of presently known configurations by providing a safe and efficient apparatus and method for administering electrolytic tissue treatment; the apparatus including an electrolytic dispensing structure that prevents DC from traveling through tissue as will be explained below.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIGS. 12A and 12B are schematic depictions of a device of the present invention with two electrodes and an electrolytic fluid pump.

FIG. 15 is a schematic depicting connection of the electrode layers of a device of the present invention to a power source. C: copper foil; P.E.: positive electrode; N.E: negative electrode; A.B.: agar bridge; I: inert.

DETAILED DESCRIPTION

Figure 1:
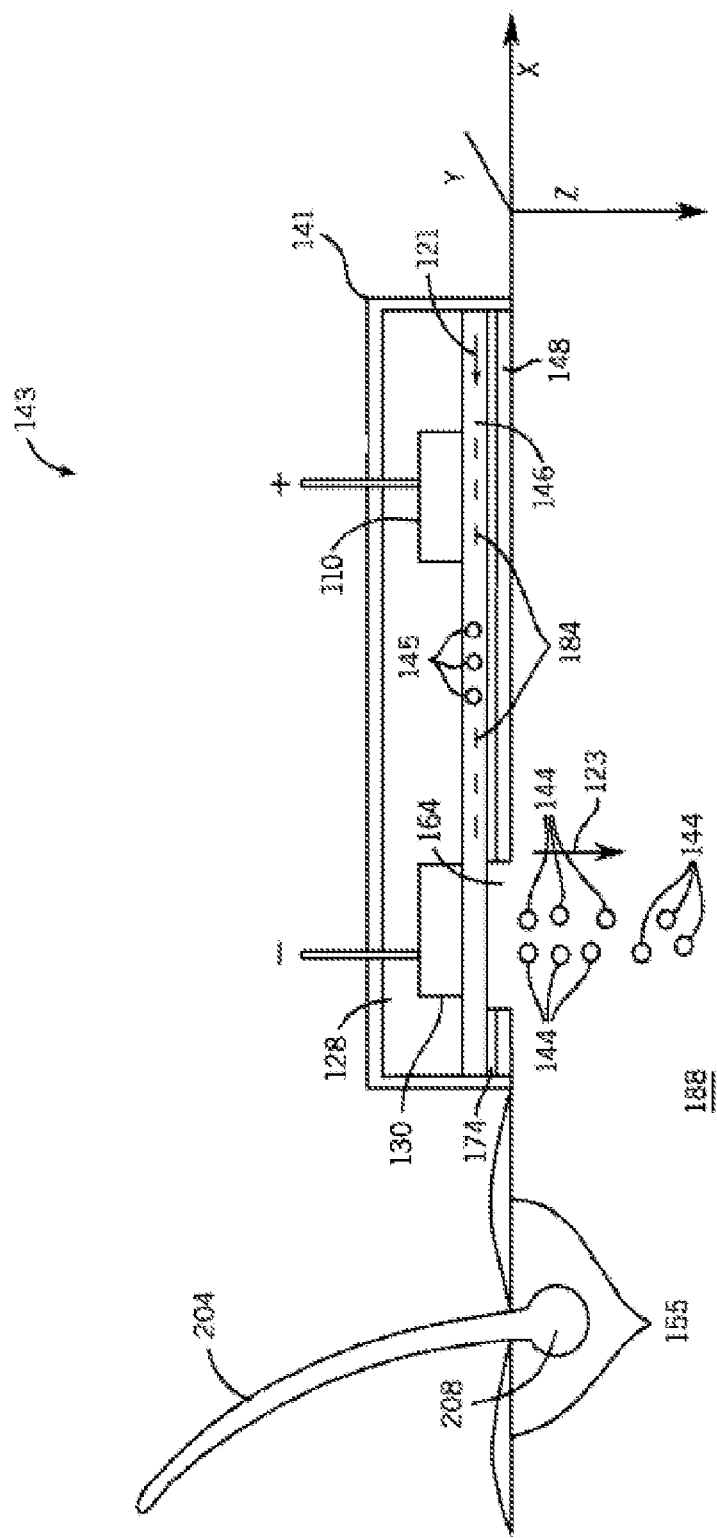
FIG. 1 is a schematic representation of an Electrolytic Conversion Device (ECD) having two electrodes, in accordance with an embodiment of the present invention.

In broad terms, the present invention relates to cosmetic and/or medical treatment of tissue using constant or pulsed DC electric current. Specifically, the present invention uses electrodes immersed in an electrolytic fluid to treat tissue, where the electrical path between the electrodes does not pass through the tissue.

It has been found that using the methods, systems and device of the present invention, that apparently a high concentration of ions produced in close proximity to a surface to be treated, such as skin, is effective in achieving a desired effect. In some embodiments, the desired effect is achieved by the contact of the products with the skin. For example, a high concentration of ions produced at an anode from a saturated NaCl solution (presumably $OH^-$ from the electrolysis of water) are effective in removing hair (apparently epilation) from skin. In embodiments, the products generate an electrochemical gradient that transports materials into or out of the skin surface to achieve the desired effect, for example, a sufficient electrochemical gradient transports a coloring material such as a dye into the skin for the purposes of tattooing.

As discussed above, a goal of the teachings of the present invention is to generate a high number of ions in a small volume of liquid in proximity to a treated surface so as to have a high ion concentration and consequently a high efficacy of treatment. At the same time, it is desired to avoid passage of current through the body of the person being treated.

The principles and operation of the teachings of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The principles, uses and implementations of the teachings of the present invention may be better understood with reference to the accompanying description, figures and examples, perusal of which allows one skilled in the art to implement the teachings of the present invention without undue effort or experimentation. In the figures, like reference numerals refer to like parts throughout.

Generally, the nomenclature used herein and the laboratory procedures utilized in the present invention include techniques from the fields of biology, engineering, material science, medicine and physics. Such techniques are thoroughly explained in the literature.

Unless otherwise defined, all technical and scientific terms used herein have the same meaning as commonly understood by one of ordinary skill in the art to which the invention belongs. In addition, the descriptions, materials, methods and examples are illustrative only and not intended to be limiting. Methods and materials similar or equivalent to those described herein can be used in the practice or testing of the present invention.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the relevant arts. Implementation of the methods of the present invention involves performing or completing selected tasks or steps manually, automatically, or a combination thereof.

Figure 7:
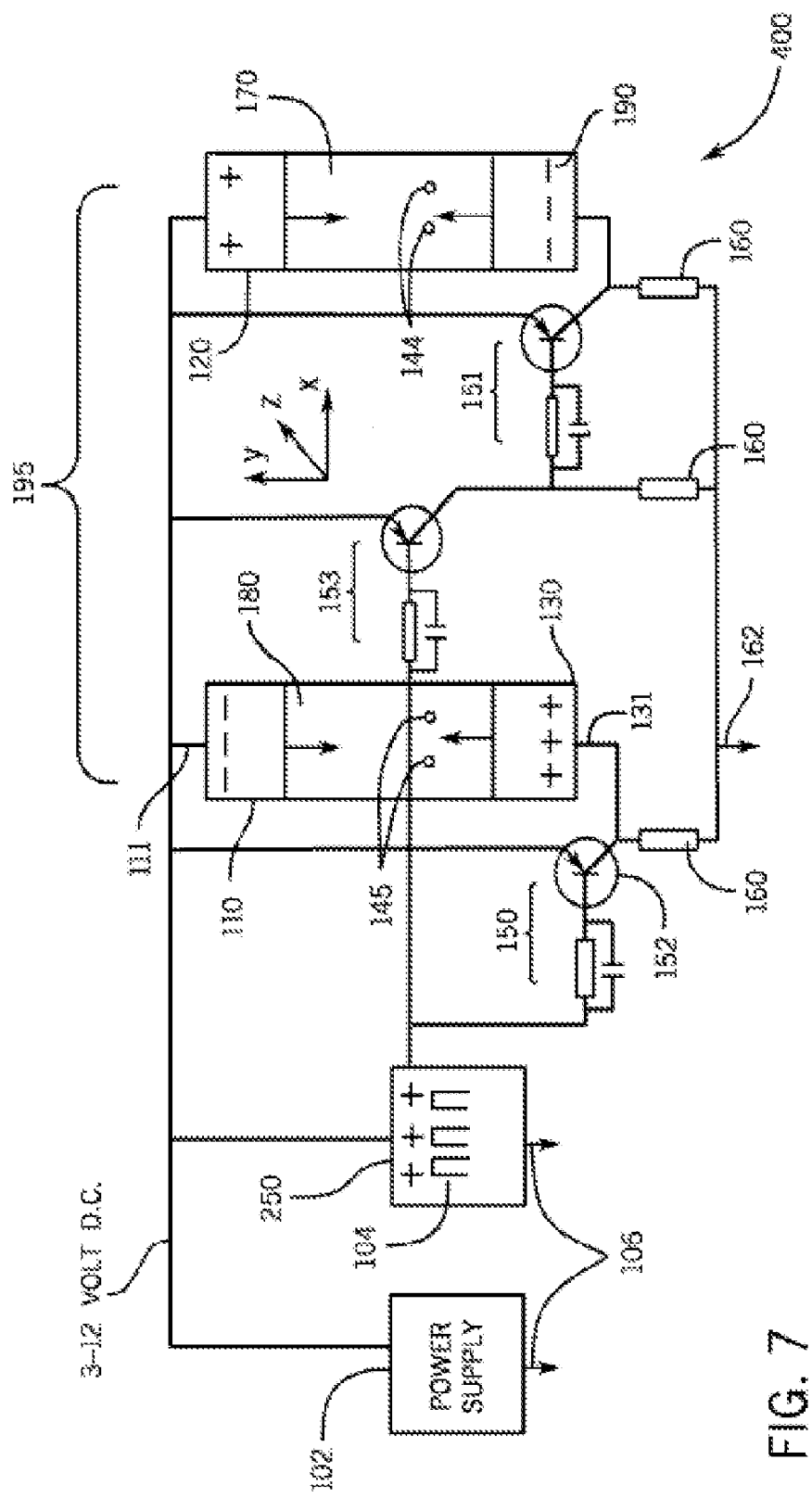
FIG. 7 is a schematic representation of an electrolytic circuit in conjunction with the ECD of FIG. 6, in accordance with an embodiment of the present invention.

The teachings of the present invention contemplate a number of embodiments including: a system 200 including a two-electrode ECD unit (depicted in FIG. 2); a system 300 including a three electrode ECD unit (depicted in FIG. 5); and a system 400 including a four-electrode ECD unit (depicted in FIG. 7).

To maintain clarity, an in-depth presentation of System 200 will be followed by structural and/or procedural differences inherent in systems 300 and 400 followed by a discussion of additional embodiments depicted in FIGS. 10, 11, 12, 13, 14 and 15. As used herein, any structure, reactant, product electrical circuitry, or current type, voltage, amperage, and/or pulse width described with reference to any embodiments (especially system 200), is applicable mutatis mutandi to the other embodiments.

Two Electrode Devices

Referring to FIG. 1, as used herein, an Electrolytic Conversion Device (ECD) refers to a three dimensional structure having at least one cathode 110, herein (+) electrode 110 and at least one anode 130, herein (−) electrode 130, to which pulsed or continuous DC is applied.

A 2-ECD 143 includes (+) electrode 110 in electrical contact with (−) electrode 130 through a fabric pad 146 saturated with a reactant 145; reactant 145 typically comprising an electrolytic solution containing a salt and/or an API.

Applying DC to electrodes 110 and 130 causes formation of ions 184 along pad 146 while an upper insulation prevents the DC from affecting other objects, for example, an operator's hand.

In an exemplary embodiment, pad 146 proximate to an opening 164 is compliant. Further, pad 146 may include or may essentially consist of one of more of a wide variety of materials, including woven cloth, non-woven cloth, fabric, fibers, spongy material, rubber, cotton, wool, polyester and polyamide.

In an exemplary embodiment, a base layer 148 comprises a thin material that, for example, is impermeable to liquid and gaseous reactants that form within electrolytic products 144. Base layer 148 comprises, for example aluminum, stainless steels, noble metal or plastic; noble metal as used herein referring to a metal from the group of stainless, non-stainless steel metals, including titanium, platinum, gold and nitinol.

Base layer 148 typically has a thickness of greater than about 15 µm and less than about 100 µm. Alternatively, base layer 148 has a thickness of greater than about 10 µm and no more than about 15 µm; the thicknesses being determined based upon current, voltage, and the location and type of tissue 188.

Base layer 148 is typically insulated from fabric pad 146 by an insulating layer 174 that comprises foil, paper, film, sheet, membrane, non-woven cloth, and/or woven cloth. Alternatively, insulating layer 174 comprises aluminum, stainless steel, noble metal, and plastic.

Alternatively, insulating layer 174 comprises materials that are gas impermeable, for example paper, polyester, polyethylene, polypropylene and silicone. In an alternative exemplary embodiment, mesh 174 comprises a material that is impermeable to gas for example produced along with reactant 144.

Mesh 174 typically has a thickness of greater than about 1 µm and less than about 5 µm. Alternatively, insulating layer 174 has a thickness of greater that 5 µm and less than 100 µm. In still other embodiments, insulating layer 174 has a thickness of greater that 100 µm.

Alternatively, mesh 174 has a thickness of no more than about 10 µm or no more than about 15 µm; the various thicknesses being determined based upon current, voltage, and tissue 188 location.

The combined thinness of base 148 and insulating 174 layers ensures that ions 184 and reactant 144 at opening 164 easily pass into tissue 188. Window 164 may include a wide variety of shapes, for example square, oval, circular, round, rectangular, curved, triangular, circular section and arced; for example depending on the shape of tissue 188 area to be treated. In an exemplary embodiment, in treating an onychomycotic nail, opening 164 could include an arced area to cover the nail curvature.

Optionally, an operator can cut opening 164 to a given shape. In an exemplary embodiment, the operator cuts through thin base layer 148 and thin insulation layer 146 to modify the shape of opening 164.

As is seen in FIG. 1, opening 164 has a portion of base layer 148 and insulation layer 146 on either side. In an alternative exemplary embodiment, opening 164 extends toward hair 204, such that opening 164 is completely unenclosed at the side nearest hair 204. In this embodiment, pad 146 may even protrude past a boundary 141 toward hair 204. Such an embodiment optionally being used on irritated tissue 188 wherein compliant pad 164 is tolerated by the recipient, but not harder base layer 148 and pad layer 146.

In an exemplary embodiment, at least a portion of pad 146 comprises a woven relatively flexible material, an amorphous relatively flexible material, or a porous, or a relatively rigid material.

Prior to application of 2-ECD 143, a liquid 155 is applied to the surface of tissue 188 to facilitate contact between tissue 188 and ions 184 at opening 164. Base layer 148 covers (+) electrode 110 and insulating layer 174, substantially preventing the (+) current from passing into tissue 188. Electrical connection between (+) electrode 110 and (−) electrode 130 is therefore substantially restricted to pad 148.

By substantially blocking the passage of current, 2-ECD 143 provides safety against associated dangerous cardiac events. The arrangement, whereby neither electrode 110 nor electrode 130 directly contact tissue 188, also stops any danger of polarization damage to tissue 188 noted above.

Even though relative safety is provided because electrodes 110 and 130 do not contact tissue, 2-ECD 143 incorporates additional features geared for patient comfort. For example heat from reactant 145 and/or products 144 is avoided in many treatments by running 2-ECD 143 at 10 mA to 300 mA.

Higher currents, for example above 1000 mA, might produce heat that could cause heating or boiling of reactant 145 and/or products 144, resulting in recipient discomfort and/or damage to tissue 188.

The rapid migration of products 144 into tissue 188 begins with electrolysis of reactant 145 as current passes through pad 146 between electrodes 110 and 130.

The electric field within pad 146 favors ions 184 to diffuse through pad 146 in a direction 121 and concentrate at opening 164. The concentration of ions 184 at opening 164 continuously rises, forming an electrochemical gradient having affinity for tissue 188, in a direction 123.

The constant movement of electrolytic products 144 and accompanying substances into tissue 188 continually depletes the supply of ions 184 at opening 164. However, ions 184 are continually produced by electrolysis of reactant 145 that occurs between (+) 110 and (−) 130 electrodes and the resulting migration of produced ions 184 to opening 164.

The electrochemical gradient, in conjunction with appropriate reactant 145, induces the movement of ions 184 through tissue 188 while accruing electrolytic activity including at least one of the above noted activities of: iontophoresis, electroosmosis, electrolytic desiccation, electokinesis, electro-epilation, and electro-onychomycotomy.

For example, in treating a mycotic nail, reactant 145 would typically consist of a topical anti-mycotic agent, for example miconazole, clotrimazole, econazole, ketoconazole, ciclopirox, naftifine, or terbinafine.

In treating cancer, reactant 145 would consist of at least one anti-cancer agent, for example anti-mitotic agents, photoreactive agents, atomic particle-emitting, antigenically tagged, or genetically altering APIs.

In treating hair 204, for example in hirsute individuals, reactant 145 would include at least one topical hair removal agent, for example thioglycolate depilatories of eflornithine. Additionally or alternatively, a Hydroxyl-ion producing reactant 145 would be used to produce (OH−) ions, as described below.

In treating actinic keratosis, reactant 145 would include at least one topical anti pre-cancerous agent, for example Jessner's solution, trichloroacetic acid, bleomycin, hydroxyurea or 5-fluorouracil (5-FU).

Additionally, in treating hyperhydrosis, reactant 145 would optionally include a sweat gland desiccant, for example an aluminum chloride-containing agent.

In an exemplary embodiment, electrolytic reactant 145 comprises an electrolytic therapeutic agent, for example an API that travels through pad 146 and tissue 188 through iontophoretic action, forming product 144 in tissue 188.

In some embodiments, for example in treating full thickness skin ulcerations, therapeutic agent 145 comprises an electrolyte desiccant that forms in tissue 188 and dries tissue 188.

Additionally or alternatively, for example an infected full thickness ulcer, reactant 145 comprises a solution containing a combination of an electrolytic agent and a separate non-charged therapeutic agent.

In some exemplary embodiments, therapeutic agent 145 travels through pad 146 and into tissue 188 through an electro-osmotic gradient induced by the electrolytic ions 184.

In some treatment embodiments, reactant 145 forms product 144, for example having substantially the same chemical formula and/or composition as reactant 145. In other embodiments, product 144 has a different formula and/or composition from reactant 145; the difference being induced, for example, through interaction with tissue 188.

Using certain agents, product 144 accumulates in the interstitial of tissue 188; herein an interstitial product 144. In other embodiments, product 144 accumulates within the cells of tissue 188; herein an intracellular product 144.

Figure 9:
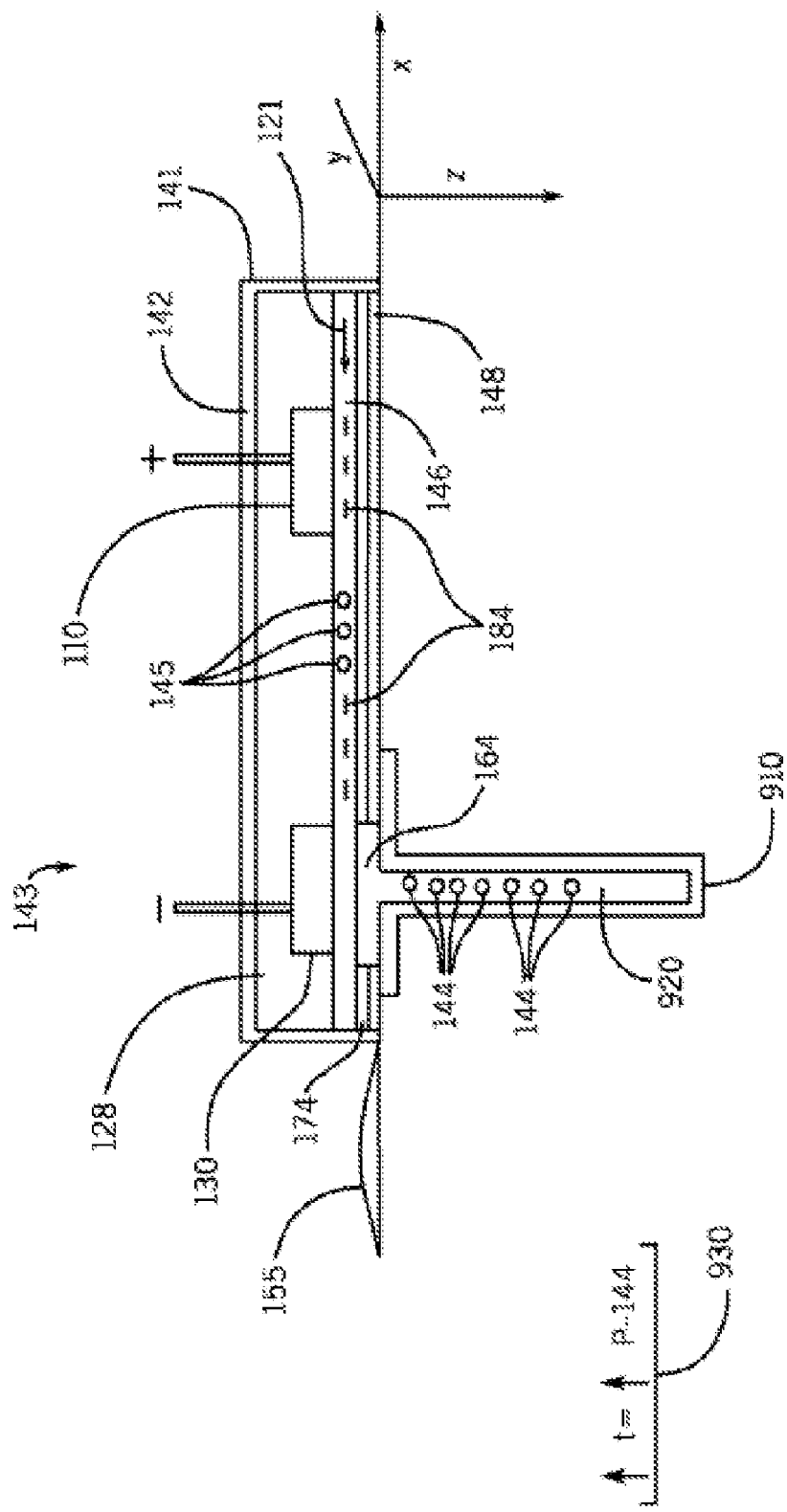
FIG. 9 is a schematic representation of a testing setup, in conjunction with the ECD of FIG. 1, in accordance with an embodiment of the present invention.

As seen in FIG. 9, a testing apparatus, built by the inventor, includes a polyester film 910 that substantially blocks a large portion of window 164 while allowing migration of electrolyte product 144 into a strip of paper 920.

Formula 930 summarizes typical results that accrued: with greater time (t) there was greater penetration (p) of products 144 into paper 920. It is hypothesized that paper 920 roughly corresponds to tissue 188 (FIG. 1). Using such an assumption, the application time of ECD-2 143 will similarly cause greater penetration of product 144 into tissue 188.

While the basis for the relationship between depth and time is not known, it is postulated that electrolytic products 144 initially are deposited in superficial areas of paper 920, corresponding to tissue 188. As electrolytic products 144 concentrate in the superficial level, the superficial level becomes substantially electrically buffered, and products 144 find a path of great electrochemical conductivity at a second, deep level. In this manner, the depth of reactant 144 is postulated to continually increase with time.

As relatively small opening 164 in cross sectional area, herein relatively small opening 164, appears to increase the speed of infusion into tissue 188. Additionally, a relatively small opening 164 appears to focus the deposition of products 144.

For example, when opening 164 is relatively small, reactants 144 form a relatively narrow column extending into tissue 188. The relationship between the size of opening 164, focus of products, and speed of deposition, allows a variety of ECD-2 143 units to be designed, each for a specific application.

For example, in hyperhydrosis treatments, described below, an enlarged opening 164 is beneficial in rapidly treating large areas of over-perspiration; and in onychomycotic treatment, described below, a specially shaped opening 164 is beneficial in focusing product 144 to the long, narrow matrix when the infection source is located within the proximal nail fold.

In some embodiments, additional housing 141, for example comprising a metal, serves to increase to strength and/or further electrically isolate 2-ECD 143, for example allowing submersion in tissue, for example in electro-hair removal and deep tumor treatment.

Embeddable ECD

Figure 8:
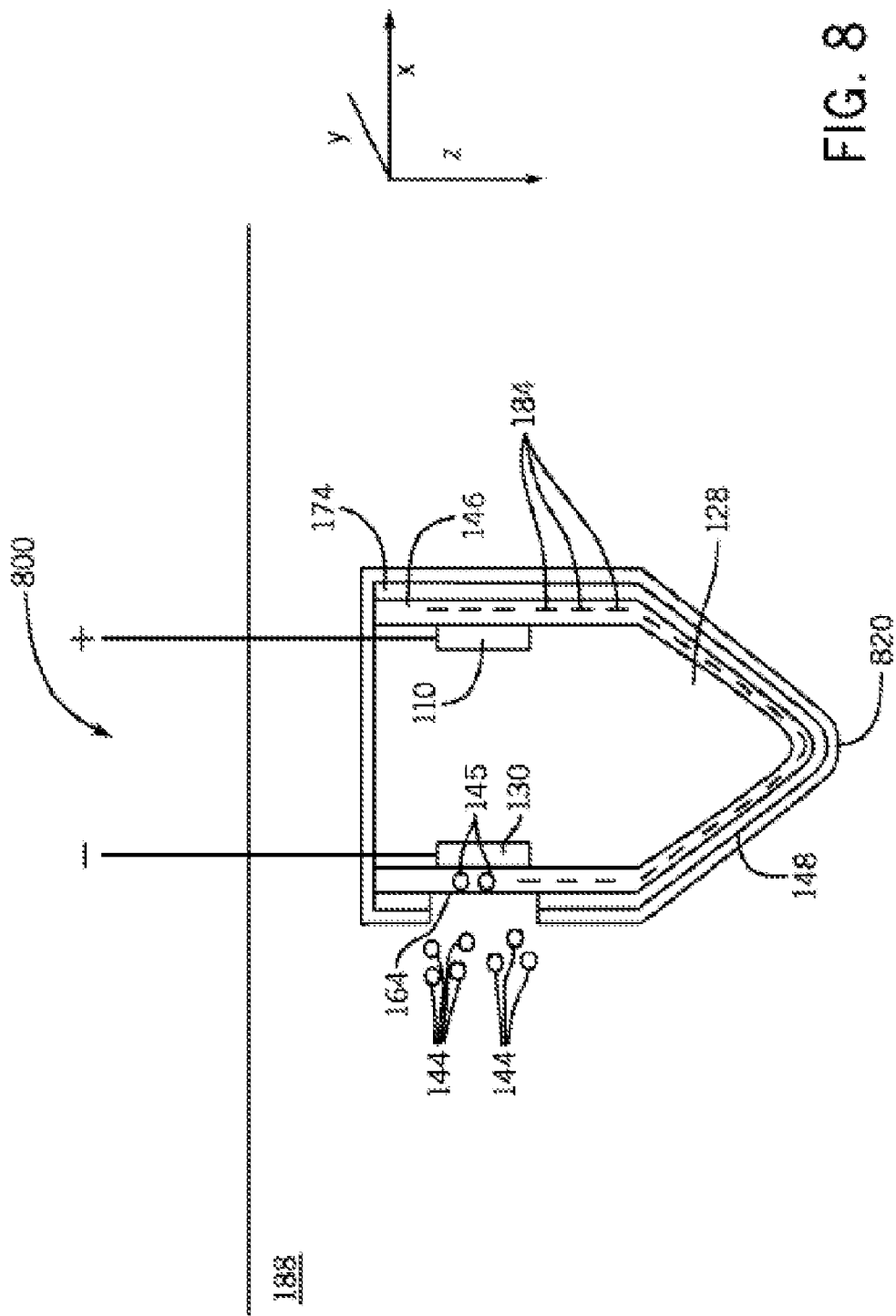
FIG. 8 is a schematic representation of an implantable ECD, in accordance with an embodiment of the present invention.

In an exemplary embodiment, as seen in FIG. 8, 2-ECD 800 includes a single, contiguous base layer 148, that allows embedding within tissue 188. Optionally, ECD-2 800 includes a tapered, or needle-like nose 820 that facilitates penetration, piercing through, and/or placement within tissue 188.

To place 2-ECD 800 in vivo, for example in internal organs such as the liver, a laparoscope is typically used along with minimal incisions; the combination of 2-ECD 800 and a laparoscope yielding fast treatment, healing and minimal post-operative scarring.

In an exemplary embodiment reactant 144 used in treating liver cancer comprises antigenically tagged anti-cancer agents. 2-ECD 800 renders tagged product 145 highly effective by causing significant and rapid concentration in the tumor tissue rather than spreading throughout tissue 188; reducing side effects resulting from less focused and/or systemic dissemination of anti-cancer APIs.

Alternatively, 2-ECD 800 can be implanted in soft tissue, bone, cartilage and fluid areas (e.g., the bladder). Optionally, at least a portion of second base layer 148 comprises aluminum, stainless steel, noble metal, or plastic.

In some embodiments, particularly those used in long-term implantation where 2-ECD 800 integrity is important; base layer 148, insulation layer 174, pad 146, and upper insulation layer 128 are of a planar laminate. Optionally, the laminated construct is substantially flexible.

Flexibility of 2-ECD 800 can be important in implantation in joints, for example the knee, when performing electrolytic treatments of cartilage ions. Due to the motion of the knee, 2-ECD 800 requires flexibility to prevent damage to a joint surface. Flexibility is also required for applications to tissue 188 having boney prominences, for example over the knee joint.

System 200

Figure 2:
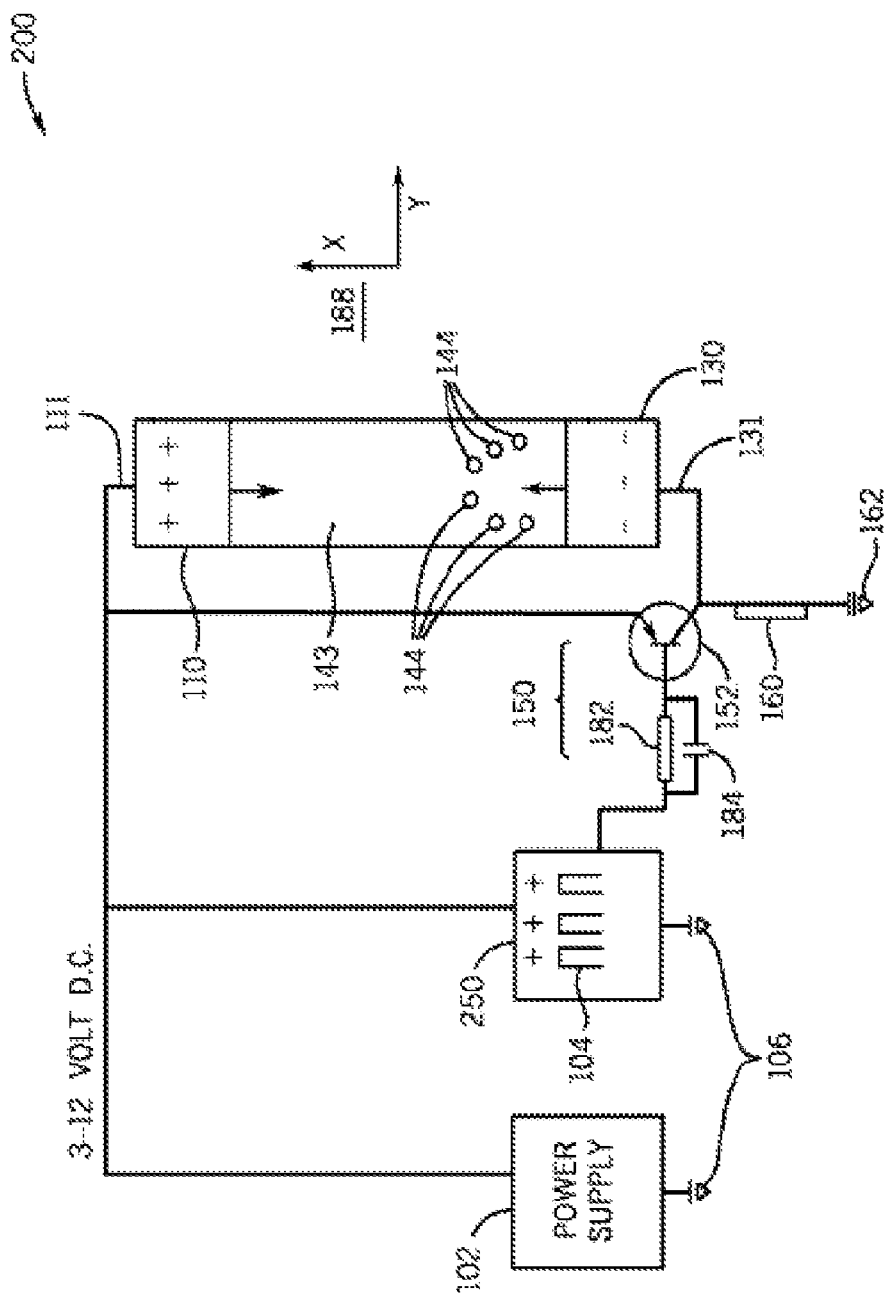
FIG. 2 is a schematic representation of an electrolytic circuit in conjunction with the ECD of FIG. 1, in accordance with an embodiment of the present invention.

As noted, in addition to continuous DC, 2-ECD 143 is capable of receiving pulsed DC as in System 200, shown in FIG. 2. In exemplary embodiments, system 200 includes a power supply 102, having a ground 106.

Power supply 102 comprises an AC to DC converter that provides at least about 1 volt; at least about 2 volts; at least about 4 volts; or at least about 6 volts. Alternatively, power supply 102 provides no more than about 40 volts; no more than about 60 volts; no more than about 80 volts; or no more than about 100 volts. Alternatively, power supply 102 comprises one or more DC batteries.

Oscillator 250 receives power from power supply 102 and, in turn, delivers an electric signal 104 comprising monopolar (+) pulses to a signal amplifier 150.

Pulsed current has, for example, a pulse width of at least about 0.1 second; at least about 0.01 second; at least about $1 \times 10^{-5}$ seconds; or at least about $3 \times 10^{-9}$ seconds.

Alternatively, pulsed current has, for example, a pulse width of no more than about 0.1 seconds; no more than about 0.01 second; no more than about $1 \times 10^{-5}$ seconds; or no more than about $3 \times 10^{-9}$ seconds.

After receiving pulsed current from oscillator 250, signal amplifier 150 amplifies current to at least about 0.1 mA, at least about 2 mA, at least about 3 mA, or at least about 4 mA.

Alternatively, signal amplifier 150, for example, amplifies current to no more than about 100 mA, no more than about 250 mA, no more than about 500 mA, or no more than about 1000 mA.

Signal amplifier 150 typically comprises: resistor 182, capacitor 184, and transistor 152; transistor 152 being connected to a resistor 160 having a ground 162.

Electrodes 110 and 130 typically are connected to terminals 111 and 131 respectively, thereby receiving current from power supply 102. Electrodes 110 and 130 typically dispense a relatively high monopolar pulsed electric current, fluctuating between 0 volts and plus (+) 3 volts. Optionally, power supply 102 fluctuates from at least about 1 volt; at least about 2 volts; at least about 4 volts; at least about 6 volts; or at least about 40 volts. Additionally, power supply 102 optionally fluctuates up to no more than about 40 volts; no more than about 60 volts; no more than about 80 volts; or no more than about 100 volts.

Variations in voltage are typically influenced by the potential ionic properties of reactant 145 (FIG. 1); the desired depth of penetration; and/or the type of tissue 188 being treated (FIG. 1).

In an exemplary embodiment, oscillator 250 is adapted to produce a pulse width comprising $1 \times 10^{-2}$ seconds to $1 \times 10^{-5}$ seconds and/or $1 \times 10^{-5}$ seconds to $3 \times 10^{-9}$ seconds.

In some embodiments, oscillator 250 forms monopolar pulses at a frequency range of between 100 kHz and 300 MHz, a range that:

a) does not stimulate nerves and muscles even at relatively high voltage; and b) facilitates significant deposition of electrolytic products 144 preferably without causing pain or tissue damage.

Additionally, the current frequency produced by oscillator 250 is optionally altered to favor concentration of products 144 at specific depths and/or structures within tissue 188.

In an exemplary embodiment, a frequency of 10 MHz is used for superficial structure treatment, for example hyperhydrosis and hair removal; 1 MHz is used for intermediate depth treatments, for example actinic keratosis; and 300 kHz is used for deep structures, for example inflammatory bursae; the latter treatment being of a depth that often involves convection flow, due to heat production.

Signal Generation

Figure 3:
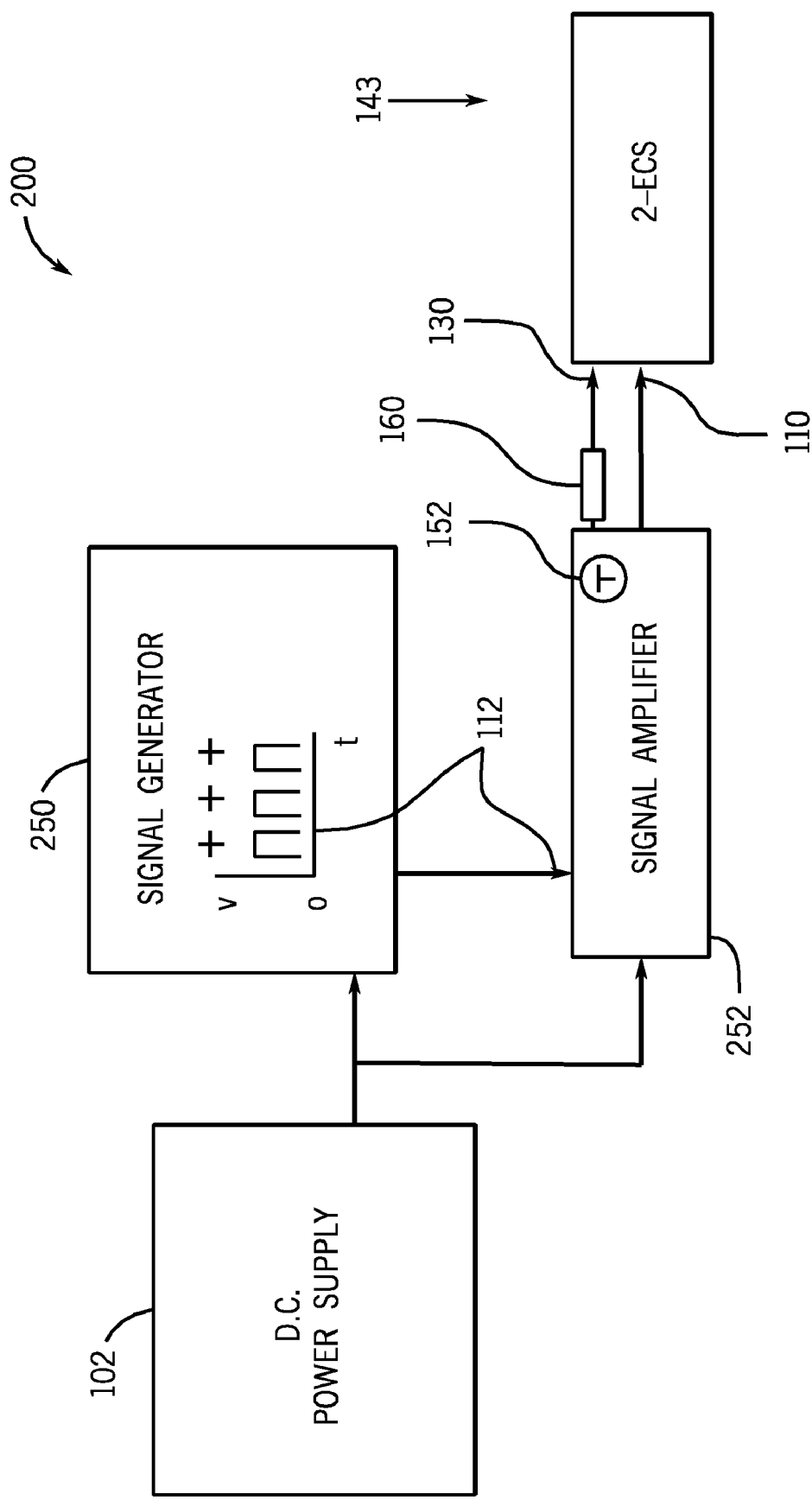
FIG. 3 is a block diagram of the circuit and Device of FIG. 2, in accordance with an embodiment of the present invention.

FIG. 3 shows a schematic diagram of System 100 in which power supply 102, comprising an AC/DC converter, supplies DC between 0 and 12 volts to signal generator 250. Signal generator 250 produces a high frequency monopolar electric signal that fluctuates between 0 and (+) 3-12 volts. The voltage is amplified at signal amplifier 252 to increase amperage to 50-300 mA and delivered to electrodes 110 and 130.

Three Electrode Devices

Figure 4:
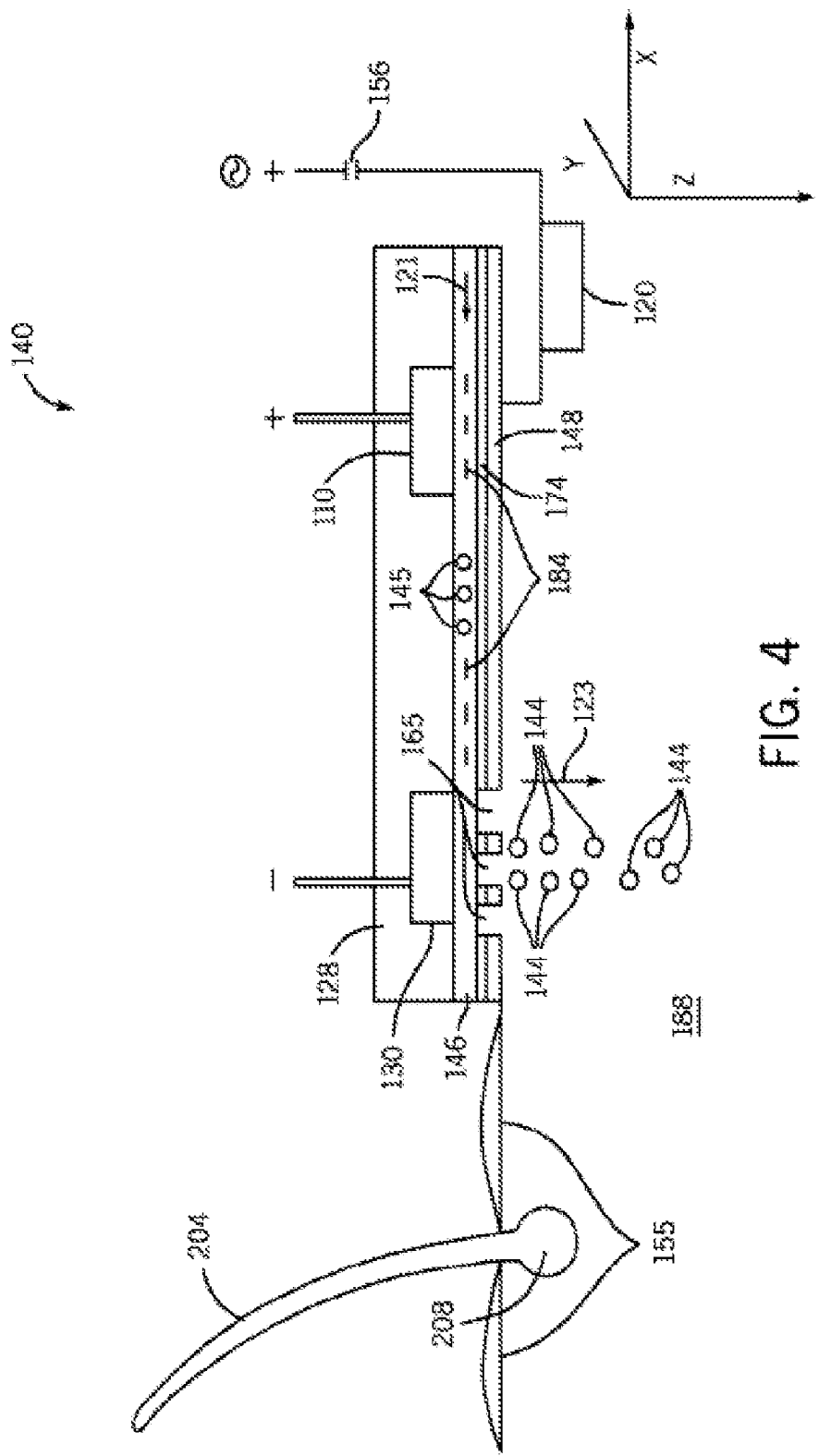
FIG. 4 is a schematic representation of an ECD having three electrodes, in accordance with an embodiment of the present invention.

Referring to FIG. 4, 3-ECD 140 includes all components of 2-ECD 143 with the addition of a side electrode 120 that is connected to a plus DC via a capacitor 156, thereby fostering the production of superficial AC Side electrode 120 producing AC appears to increase kinetic movement of product 144, thereby aiding in deposition of product 144.

In an exemplary embodiment, AC from side electrode 120 appears to enhance deposition of product 144 while remaining primarily on the surface of tissue 188. It is postulated that for this reason AC from side electrode 120 appears to function without negatively impacting the chemo-electric gradient in tissue 188 or the deposition of electrolytic product 144.

System 300

Figure 5:
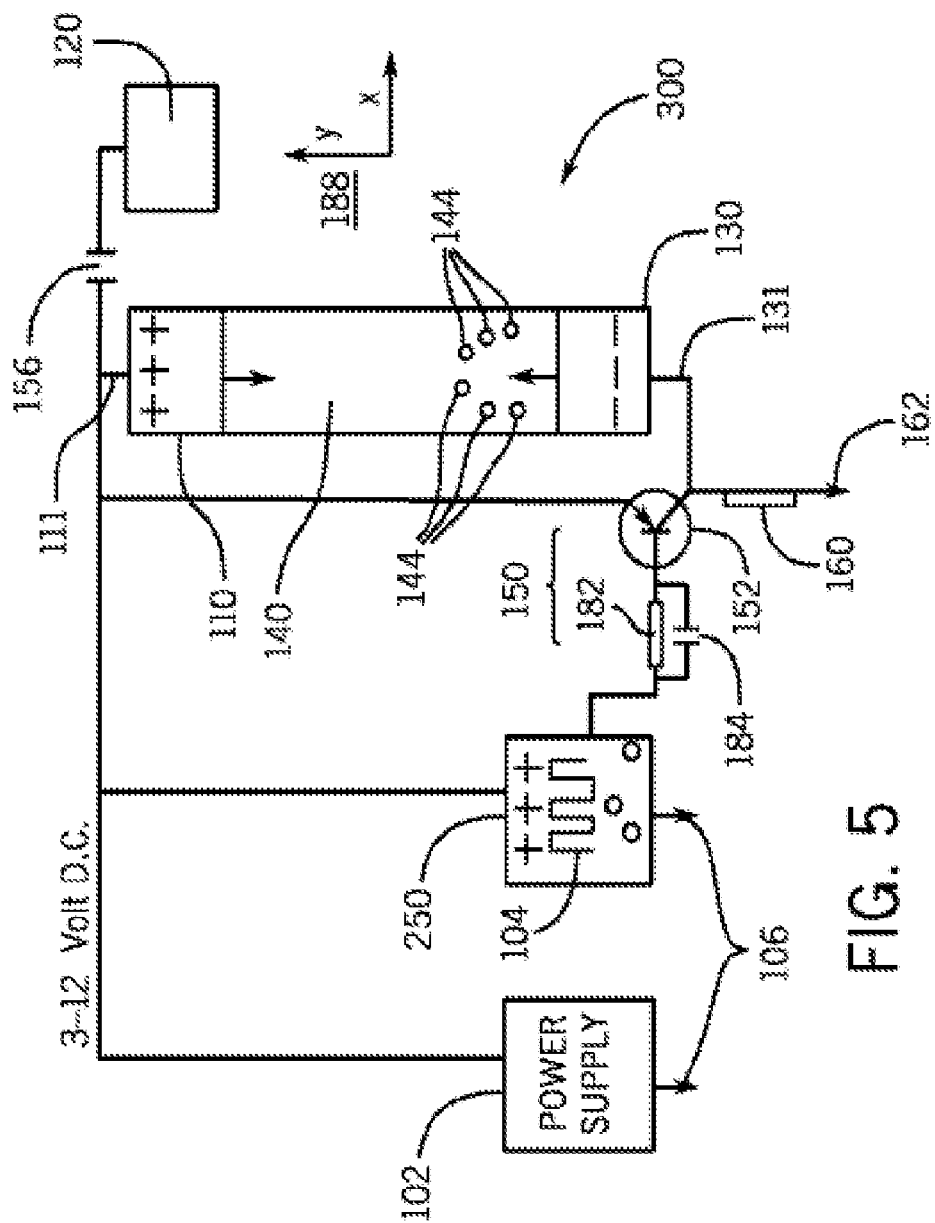
FIG. 5 is a schematic representation of an electrolytic circuit in conjunction with the ECD of FIG. 4, in accordance with an embodiment of the present invention.

Referring to FIG. 5, system 300 uses substantially the same circuitry as that of 2-ECD 143 (FIG. 2), with the addition of side electrode 120 connected to (+) current through a capacitor 156.

The net effect of current flow to side electrode 120 appears to produce a mild superficial AC that enhances tissue absorption. System 300 appears to have promise in transdermal API delivery, providing increased API penetration and treatment speed.

Four Electrode Device

Figure 6:
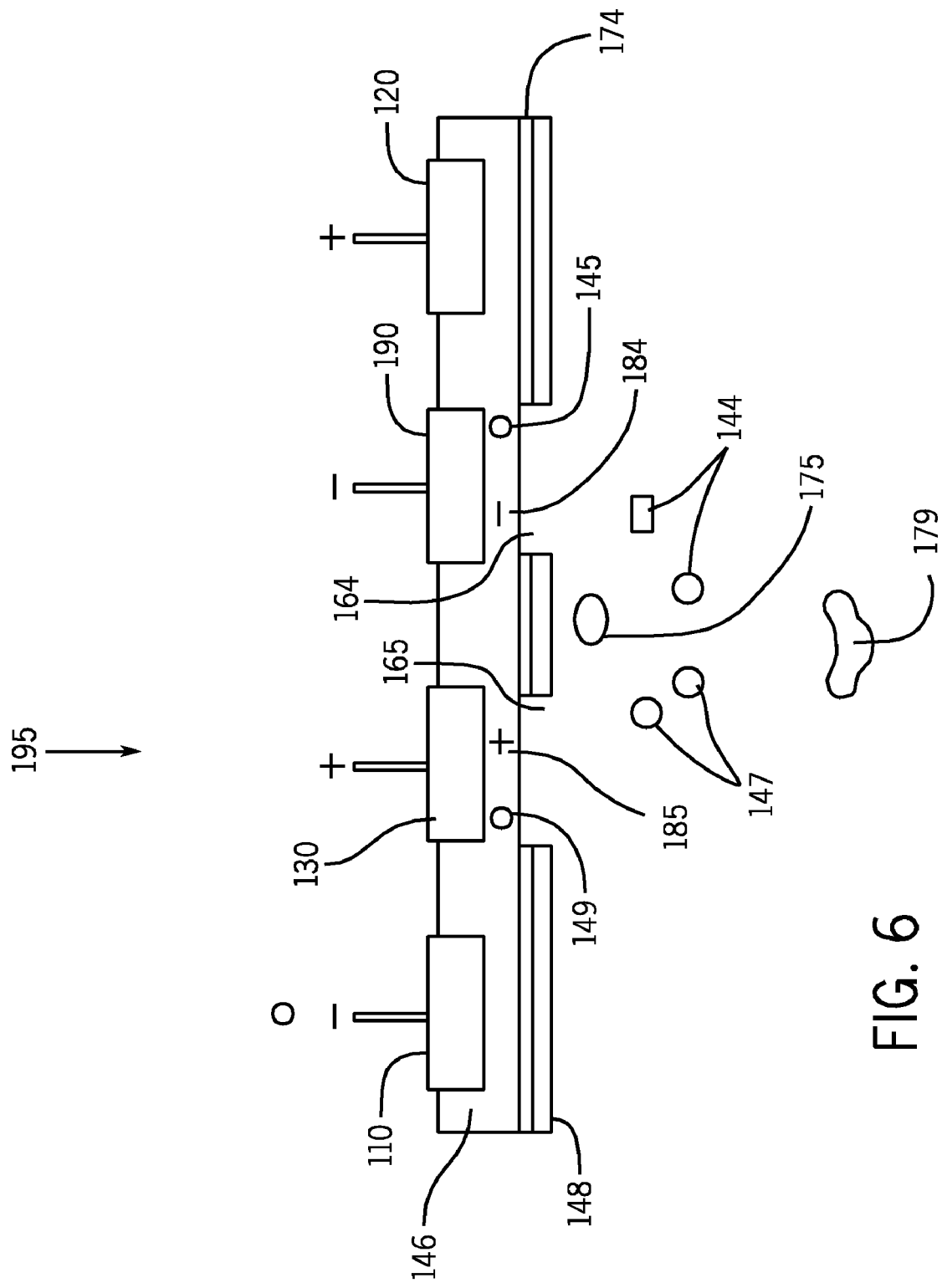
FIG. 6 is a schematic representation of an ECD having four electrodes, in accordance with an embodiment of the present invention.

Referring to FIG. 6, 4-ECD 195, includes two sets of (+) and (−) electrodes:

First (+) 130 and second (−) 110 electrodes in a first set; and
Third (+) 120 and fourth (−) 190 electrodes in a second set.

In some exemplary embodiments:

(+) electrode 130 is positioned over an opening 165, forming (+) ions 185 and electrolytic products 147 from a reactant 149; and third (+) electrode 120 is positioned over opening 164, forming (−) ions 184 and electrolytic products 145 from reactant 145.

The above-noted arrangement is useful, for example, when two products 144 and 147 having opposite polarity are used in the same treatment.

Alternatively, when treatment requires two products 144 and 147 having, for example, the same polarity, but that need to combine in tissue 188, (−) electrodes 110 and 190 are positioned over openings 165 and 164 respectively.

In still another embodiment, pads 170 and 180 (FIG. 7) have the same polarity, but the electrical potential of pad 170 is different from the electrical potential of pad 180. In an exemplary embodiment, a third reactant 175 is used in this latter embodiment in which reactant 175 comprises a catalyst that serves to activate products 144 and 147.

Optionally, catalyst 175 additionally has electrokinetic properties and is introduced onto tissue 188, for example by injection. As defined above, an electrokinetic substance responds to differences in electrical potential.

In an exemplary embodiment, products 144 and 147 are deposited in two separate areas and, for example, diffuse toward one another. At the same time, an electrokinetic catalyst product 179 is deposited in a third area, for example between products 144 and 147 so that as all three products 175, 144 and 147 combine, catalyst cause products 144 and 147 to catalyze into product 179.

Implementation of the three-product migration scenario noted above is useful, for example, in treating brain lesions in which catalyzed products will not pass through the blood brain barrier (BBB). By introducing precursor reactants that pass through the BBB, and applying 2-ECD 400, to a topically accessible area of the brain, for example the brain stem, reaction takes place within brain tissue and supplies necessary reactant 145 including the necessary therapeutic entities.

System 400

Referring to FIG. 7, system 400 is a schematic depiction of circuitry that includes 4-ECD 195. Similar to prior systems, gateway 150 distributes DC pulses to electrodes 110 and 130 on a Device portion 180. A second gateway 151 distributes DC pulses to electrodes 120 and 190 on a second Device portion 170.

Additionally, a third gateway 153 is positioned between portions 180 and 170 to ensure separation of the currents, pulse width and voltage so that each of portions 180 and 170 function independently. Alternatively, gateway 153 causes a shift of in pulse so that when current pulse is present at 180, at 170 the pulse is absent, and vice versa.

Four additional embodiments of devices of the present invention are depicted below, the devices being exceptionally suited for topical treatment of a surface such as the skin, for example for cosmetic treatments such as hair removal or pore cleaning or for therapeutic treatments such as topical application of suitable APIs. In such devices, there is a conduit that allows an electrolytic fluid to flow from a reservoir to a contact surface, where the electrodes are functionally associated with the conduit so that the desired electrolysis products are produced in an effective concentration at the contact surface. Although such devices may be used in various ways, including as described above, the devices are exceptionally suited for treatment of a surface. When the contact surface is rubbed across a surface to be treated, electrolytic fluid containing electrolysis products at the contact surface contacts the treated surface leading to a desired effect. Such a device is generally also effective when held statically and there is no flow through the conduit. It has been found that when rubbed across a surface, a flow rate of between about 10 microliters minute$^{-1}$ and 100 microliters minute$^{-1}$ is effective.

Typically, the first electrode which is of the polarity that produces the products that provide the desired effect are as close as possible to the aperture where the conduit emerges through the contact surface. As it is desirable to have a high concentration of electrolysis products, a first electrode of such a device is advantageously configured to be as close as possible to the contact surface and is designed to perform electrolysis in a small a volume of fluid as possible.

Typically, the second electrode is as close as possible to the first electrode so as to reduce resistance between the electrodes, but not to close in order to reduce efficient migration of different polarity electrolysis products produced at the different electrodes towards each other.

Further, during use of a device the flow of electrolytic fluid through the conduit may in some instances carry produced electrolysis products from the second electrode to the first electrode. To reduce this usually undesirable effect, in embodiments a flow barrier is interposed between the first electrode and the second electrode. A flow barrier is configured to allow the passage of ions therethrough but to prevent the flow of electrolytic fluid. Typical flow barriers include agar agar or suitable membranes.

As discussed above, it is desirable to avoid or reduce to as great an extent possible flow of current through the body of a treated person. In embodiments this is achieved by ensuring that the aperture of the conduit is as small as possible and as much as possible blocked by the first electrode, that is to say, fluid flowing therethrough is forced to pass as close as possible to the surface of the first electrode. Typical configurations include a slot shaped aperture surrounded by a first electrode, or an aperture made of one or more holes, each hole surrounded by a first electrode.

Device 500

Figure 10A:
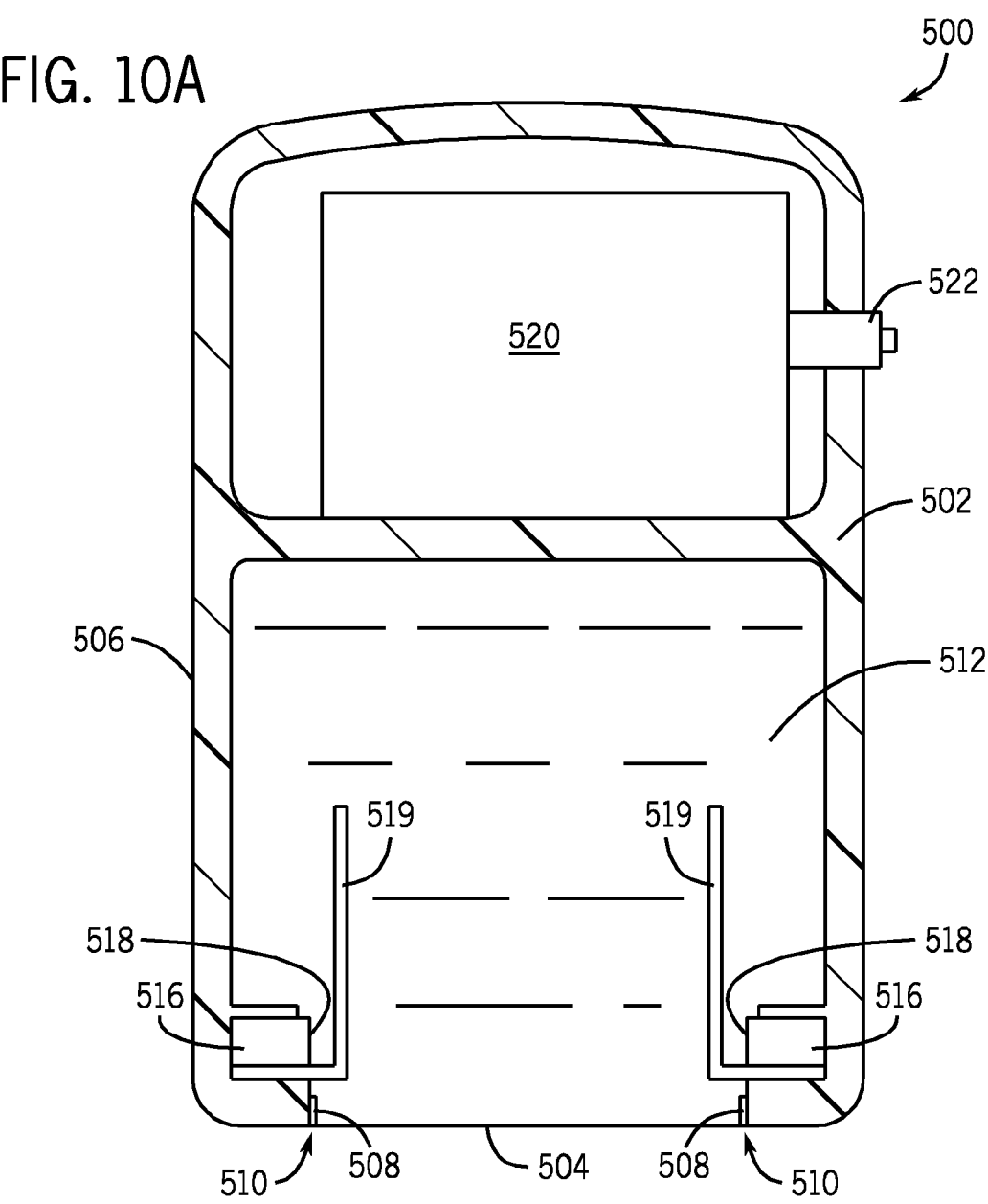
FIGS. 10A and 10B are schematic depictions of a device of the present invention with two electrodes and an absorbent electrolytic fluid reservoir.
Figure 10B:
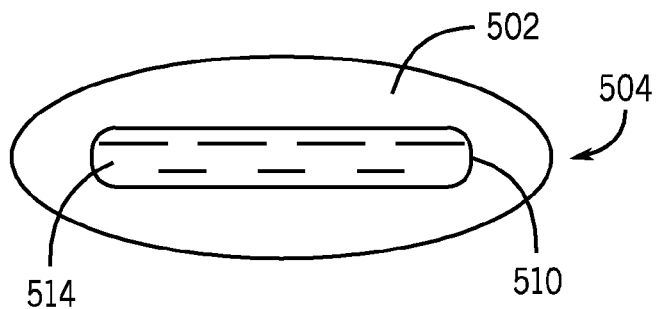

A further embodiment of the present invention, device 500 is depicted in side cross section in FIG. 10A and from the bottom in FIG. 10B.

Elongated portable housing 502 of device 500 is made of a number of components of vacuum formed high impact polystyrene. A contact surface 504 is positioned at an end of portable housing 502. Curved walls 506 substantially perpendicular to contact surface 504 define rounded holding surfaces, allowing device 500 to be easily held in one hand while rubbing contact surface 504 against a surface.

On the inside rim of contact surface 504 is located an elongated ring-shaped first electrode 508 made of silver with an electrode face 510 covered with carbon, so that the rim of an electrode face 510 of first electrode 508 comprises a portion of contact surface 504. The breadth of the ring on contact surface 504 is about 0.1 mm, the width (A-A) of first electrode 508 and consequently electrode face 510 apparent on contact surface 504 is about 35 mm, and the height of first electrode 508 is about 1 mm, giving face 510 of first electrode 508 an area of about 70 mm$^2$. The elongated shape of first electrode 508 is such that the hole through first electrode 508 is substantially a 100 micrometer slit.

Contained within portable housing 502 is reservoir 512 an absorbent body of felt impregnated with an electrolytic fluid. Conduit 514 is a piece of felt continuous with reservoir 512 that emerges from contact surface 504 flush with and contacting first electrode 508 and in part defining contact surface 504. The terminal portion of conduit 514 is encircled by first electrode 508. The width of the terminal portion of conduit 514 (about 35 mm) and the width of first electrode 508 is substantially similar.

Also contained within portable housing 502 is an elongated-ring shaped second electrode 516 made of a silver with an electrode face 518 covered with carbon that firmly contacts the felt material of conduit 514. The height of second electrode 516 is approximately 6 mm so that the area of face 518 of second electrode 516 is approximately 500 mm$^2$. The hole through second electrode 516 is relatively large being about 10 mm wide. The closest portion of face 518 of second electrode 516 is about 2.5 mm from face 510 of first electrode 508.

Physically interposed between first electrode 508 and second electrode 516 is flow barrier 519, substantially a hard polystyrene sleeve with holes with an L-shaped cross-section that fits inside the bore of second electrode 516 that divides reservoir 512 into two parts: an inner portion that is in fluid communication with first electrode 508 and a peripheral portion that is in fluid communication with second electrode 516. Holes in flow barrier 519 are covered with a material, for example of agar agar impregnated fabric, that are permeable to ions. In such a way, there is an electrical connection between first electrode 508 and second electrode 516 through flow barrier 519, but flow of electrolytic fluid is prevented.

Also contained within portable housing 502 is DC power supply 520 (four 1.5V batteries) functionally associated with on/off switch 522 that together with wires acts as a power inlet that provides electric power from DC power supply 520 to first electrode 508 and second electrode 516.

For use, on/off switch 516 is set to an "ON" state so that electrolysis of components of electrolytic fluid occurs while contact surface 504 of device 500 is moved across a surface (e.g., skin) to be treated. In the manner of prior art felt-tip pens, electrolytic fluid is transferred by capillary action from reservoir 512 through conduit 514 to be applied to the surface by contact surface 504. A high concentration of ions are produced in the immediate proximity of first electrode 508, both in the film of electrolytic liquid between the surface and contact surface 504, and inside the terminal end of conduit 514 near contact surface 504. It is important to note that in device 500, face 510 of first electrode 508 is functionally associated with conduit 514 in that fluid emerging from conduit 514 onto contact surface 504 makes an electrical connection between first electrode 508 and second electrode 516 through electrolytic fluid in conduit 514.

Device 524

Figure 11A:
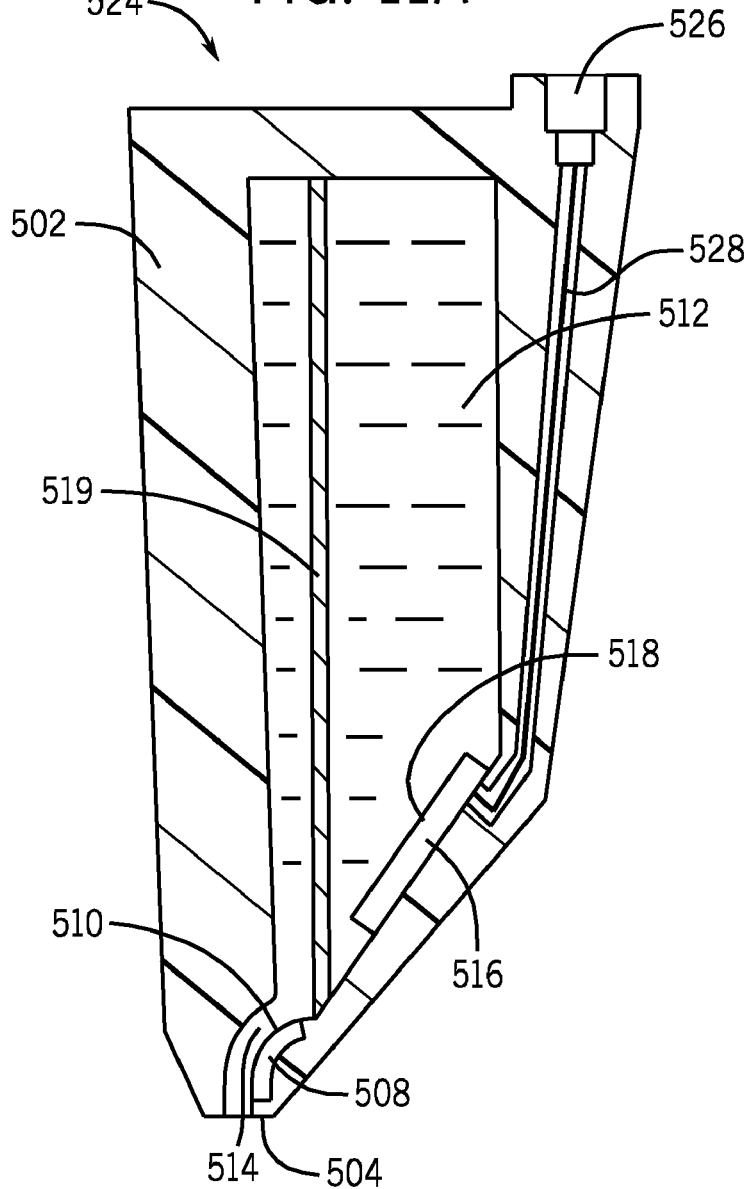
FIGS. 11A and 11B are schematic depictions of a device of the present invention with two electrodes and a capillary passage electrolytic fluid conduit.
Figure 11B:
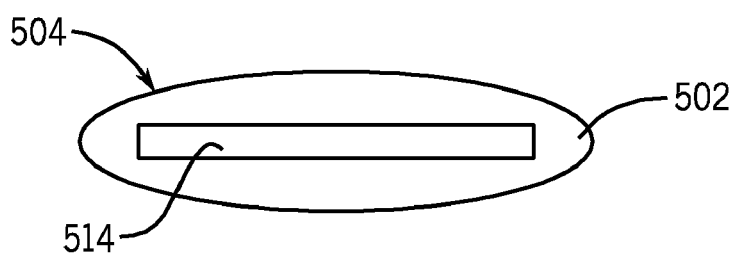

A further embodiment of the present invention, device 524 is depicted in side cross section in FIG. 11A and from a bottom view in FIG. 11B.

As in device 500, portable housing 502 of device 524 is made of a number of components of vacuum formed high impact polystyrene and includes a contact surface 504 at one end. Contained within portable housing 502 is reservoir 512 a void configured to contain an electrolytic fluid. Conduit 514 comprises a broad capillary passage (35 mm) that narrows in cross section and provides fluid communication from reservoir 512 to the outside through contact surface 504. Proximate to where conduit 514 emerges at contact surface near first electrode 508 conduit 514 is narrow, about 100 micrometers but in the region between first electrode 508 and second electrode 516 conduit 514 is broad, about 600 micrometers.

Inside conduit 514 and proximal to contact surface 504 is positioned first electrode 508 (a 1 mm broad by 35 mm wide carbon coated silver electrode) so that face 510 of first electrode 508 comprises, in part, the wall of conduit 514. The closest end of face 510 of first electrode 508 is 0.2 mm from contact surface 504.

Inside conduit 514, further from contact surface 504 than first electrode 508 and 2 mm therefrom is positioned second electrode 516 (a 6 mm broad by 35 mm carbon coated silver electrode) so that face 518 of second electrode 508 comprises, in part, the wall of conduit 514.

To prevent the flow of electrolytic fluid between first electrode 508 and second electrode 516 without breaking the electrical connection therebetween, a sheet of agar agar impregnated fabric as a flow barrier 519 is attached to the wall of conduit 514 between the two electrodes and is secured upwards in such a way as to divide reservoir 512 into two parts.

Device 524 is devoid of an integral power supply. Rather, device 524 is provided with a jack 526 configured together with wires 528 acts as a power inlet to provide electrodes 510 and 516 with power from an external power supply.

The use of device 524 depicted in FIGS. 11A and 11B is substantially similar to the use of device 500 depicted in FIGS. 10A and 10B with a few noteworthy differences. As device 524 is devoid of an integral power supply, power is externally provided through jack 526 by an external power supply (not depicted). Further, electrolytic fluid is not transported to a surface in the manner analogous to a felt tip pen by contact with a tangible conduit, but rather in the manner of a fountain pen through a capillary passage.

Device 530

A further embodiment of the present invention, device 530 is depicted in side cross section in FIG. 12A and from a bottom view in FIG. 12B.

As with device 500, portable housing 502 of device 530 is made of a number of components of vacuum formed high impact polystyrene and includes a contact surface 504 at one end.

Contained within portable housing 502 is reservoir 512 a void configured to contain an electrolytic fluid 532. Reservoir 512 is provided with a port 534 and a pressure equalizing passage 536 for charging reservoir 512 with electrolytic fluid 532. Port 534 is sealable with the help of cap 538.

Contained within portable housing 502 is a rectangular (35 mm wide by 20 mm broad) second electrode 516 made of silver with an electrode face 518 coated with carbon.

First electrode 508 is comprises a 0.1 mm thick stainless steel mesh, the surface of which defines face 510 of electrode 508. Coating the bottom of the steel mesh is a 0.1 mm thick layer of high impact polystyrene that defines contact surface 504 and is perforated to form a plurality of holes 540.

When device 530 is properly assembled, face 510 of electrode 508 is 2.5 mm from the surface of second electrode 516, defining a chamber 35 mm wide, 4 mm broad and 2.5 mm high. Conduit 514 of device 530 comprises the bore of holes 540 and the chamber between second electrode 516 and the component including first component 508, having an approximate total volume of 350 mm$^3$. Electrolytic fluid 532 is transported from reservoir 512 into conduit 514 by pump 542 (a peristaltic pump from Instech Laboratories, Inc., Plymouth Meeting, Pa. USA) at an appropriate rate (in embodiments, between about 100-1 ml minute$^{-1}$).

To prevent the flow of electrolytic fluid between first electrode 508 and second electrode 516 without breaking the electrical connection therebetween, a sheet of agar agar impregnated fabric as a flow barrier 519 is attached so as to divide the chamber between the two electrodes into two.

Also contained within portable housing 502 is DC power supply 520 (4 1.5V batteries) functionally associated with on/off switch 522 that together with wires 528 acts as a power inlet that provides electric power from DC power supply 520 to first electrode 508, second electrode 516 and pump 542.

The use of device 530 depicted in FIGS. 12A and 12B is substantially similar to the use of device 500 depicted in FIGS. 10A and 10B and device 524 depicted in FIGS. 11A and 11B with a noteworthy difference that pump 542 is used to transport electrolytic fluid 532 though conduit 514.

Device 544

Figure 13A:
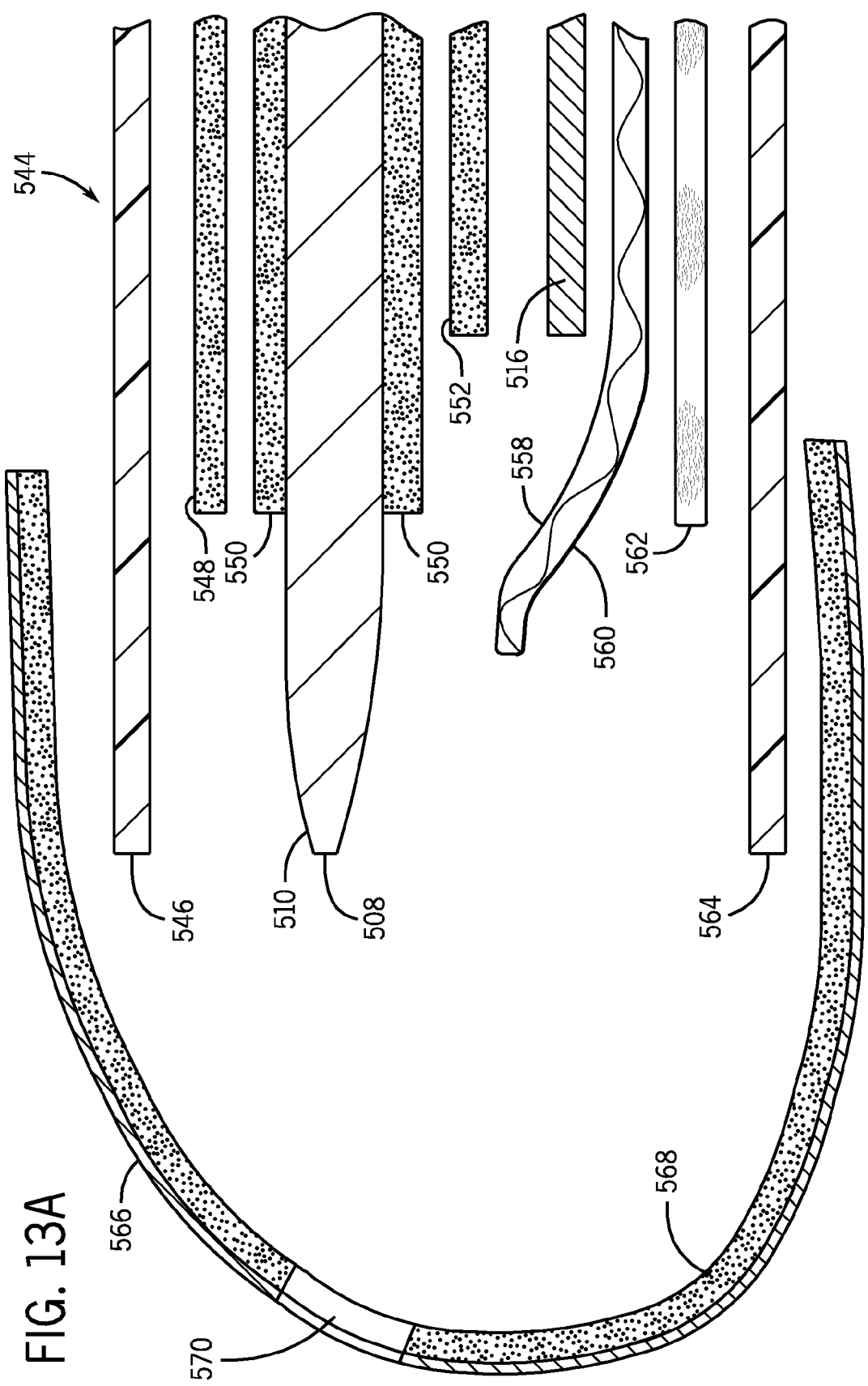
FIGS. 13A and B is a schematic depiction of a device of the present invention that is substantially a laminated device.

A further embodiment of the present invention, device 544 is depicted in side cross section in FIGS. 13A and B, was assembled and tested.

Device 544 is substantially a multilayered device. In FIG. 13A the device is depicted in exploded cross section. From top to bottom, the layers of device 544 are:

layer 546, a 100 micrometer thick polyester sheet (PPC film for overhead projectors from Juliver, Netanya, Israel);

layer 548, a 100 micrometer thick double sided adhesive sheet (30 micrometer polyester with a 35 micrometer thick adhesive layer on either side DS polyester supplied by Ritrama S.p.A., Caponago, Italy);

first electrode 508 including a wire lead (not depicted) that is substantially a 35 mm wide by 10 mm long sheet of 300 micrometer thick stainless steel where a 35 mm side is sharpened to 100 micrometer coated on all layers with a 100 micrometer thick layer of thermoplastic adhesive 550 (Bostick® Thermogrip® 6323 glue stick from Bostick Findley, Inc. Middleton Mass., USA). Adhesive 550 was removed to expose 2.5 mm of a 35 mm sharpened width of first electrode 508 as an electrode face 510;

layer 552, a 100 micrometer thick double sided adhesive sheet (30 micrometer polyester with a 35 micrometer thick adhesive layer on either side, DS polyester supplied by Ritrama S.p.A., Caponago, Italy);

second electrode 516, a 100 micrometer thick TENS/EMS electrode (KM-PT24 cut to size, Kappa Medical, Prescott, Ariz., USA) including a wire lead (not depicted);

layer 558, a 100 micrometer thick sheet of absorbent nonwoven fabric (Photex Scanner Wipes, BBA Fiberweb, Simpsonville, S.C., USA) heat laminated to sheet 560 of 100 micrometer thick of polyethylene;

layer 562, a 100 micrometer thick double sided adhesive sheet (30 micrometer polyester with a 35 micrometer thick adhesive layer on either side, DS polyester supplied by Ritrama S.p.A., Caponago, Italy);

layer 564, a 100 micrometer thick polyester sheet (PPC film for overhead projectors from Juliver, Netanya, Israel); and layer 566, a 10 micrometer thick aluminum foil layer backed with layer 568, a 100 micrometer thick double sided adhesive sheet (30 micrometer polyester with a 35 micrometer thick adhesive layer on either side, DS polyester supplied by Ritrama S.p.A., Caponago, Italy).

A row of 3 millimeter holes 570 separated by 1 mm are made in layers 566 and 568.

Figure 13B:
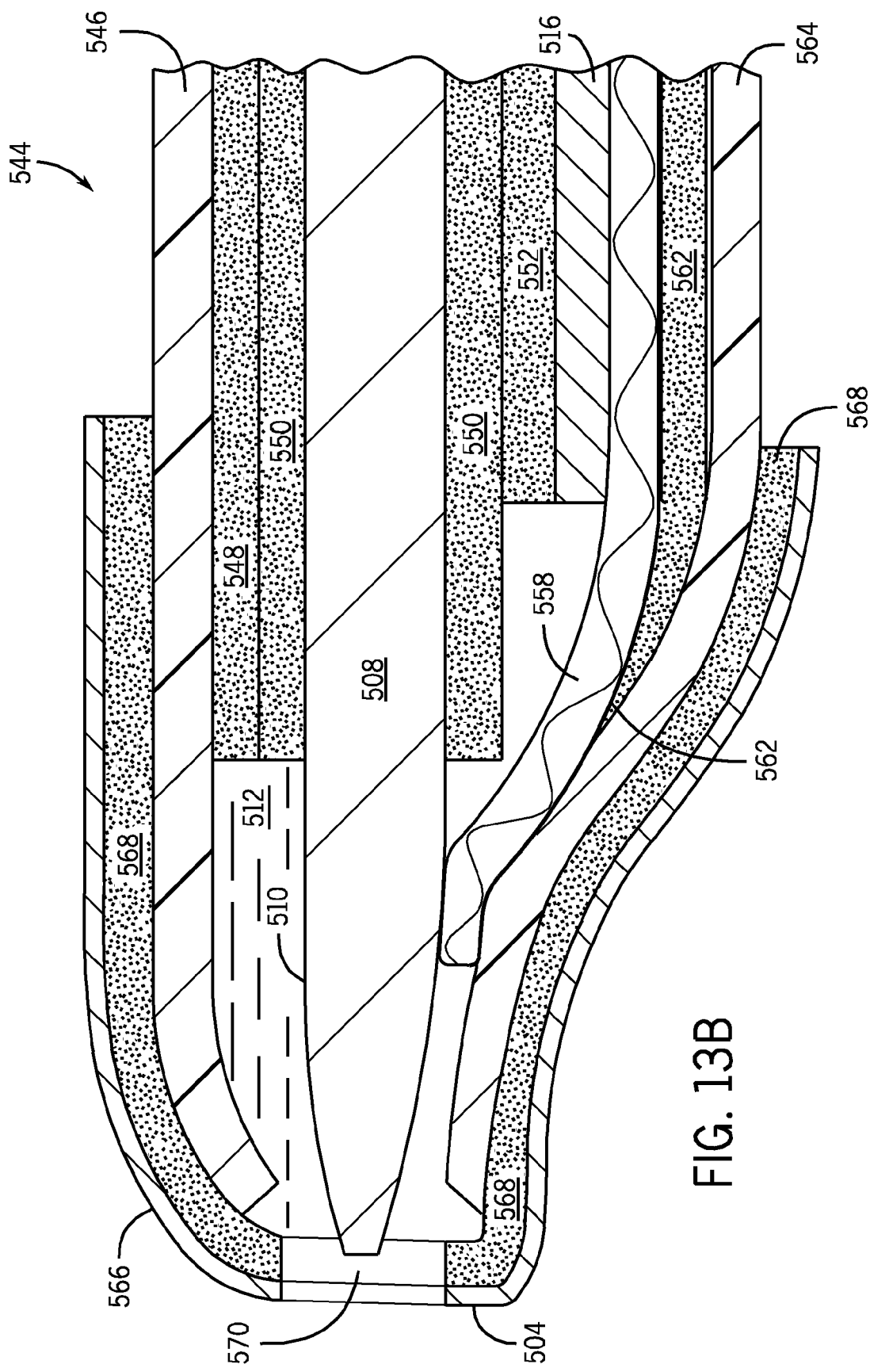

The layers were pressed together and layer 568 attached to layers 546 and 564 to produce a device as depicted in FIG. 13B where layers 546 and 564 are substantially flush with the tip of first electrode 508, layers 548, 550 and 562 are recessed by 2.5 mm and cloth layer 558 (when soaked with an electrolyte solution) provides electrical contact between first electrode 508 and second electrode 516. The volume defined between layer 568 and electrode face 510, together with absorbent sheet 558 constitute an electrolytic fluid reservoir 512 of device 544. First electrode 508 contacts sheet 568 along the line defined by holes 570. Layer 566 defined contact surface 504.

For use, fabric layer 558 was charged with a saturated NaCl water solution from the far side of the device (not depicted) until no more solution could be absorbed.

The leads of electrodes 508 and 516 were attached to an external power supply so that first electrode 508 functioned as an anode and 100 mA at 9V, as measured by a multimeter, was applied between electrodes 508 and 516 providing 1.25 mA per mm$^2$ area of electrode face 510 of first electrode 508. It is estimated that the distance from 510 face of first electrode 508 to contact surface 504 of device 544 was about 110 micrometers, the combined thickness of layers 566 and 568.

Contact surface 504 of device 544 was dipped in a bath of electrolytic solution so that the electrolytic solution would fill electrolytic fluid reservoir 512. Contact surface 504 of device 544 was passed along a hirsute thigh of an adult male subject at a rate similar to a slow but normal shaving rate when using a two bladed razor. After every few strokes, the end of device 544 was again dipped in a bath of electrolytic solution to replenish the reservoir. Some hair was observed to fall out in minutes and the treated area was observed to be substantially hairless by the end of a week. The hairless state remained for a period of months after a single treatment, indicating true epilation.

Although not wishing to be held to any one theory, it is currently believed that the electricity passing between electrodes 510 and 516 lead to electrolysis of components of the electrolytic solution generating electrolysis products such as OH$^-$ in the area of face 510 of first electrode 508. Due to the construction of the device, the electrolysis occurred in a small volume of fluid so that the concentration of electrolysis products was high enough so that sufficient products migrated through holes 570 to damage the hair roots and consequently lead to the observed epilation.

Device 600

A further embodiment of the present invention, Device 600, is depicted in FIGS. 14A-14H. Device 600 is substantially a multi-layered device with each layer being substantially planar. Device 600 is shown with three negative electrode layers and two positive electrode layers; however, embodiments using more or fewer electrode layers are also embodied herein. Similar to other devices and apparatus described herein, the Device 600 is useful for cosmetic and/or therapeutic tissue treatments. For example, the devices may be used for epilation and/or treatment of any of a number of the skin conditions described above (e.g., cancer, pre-cancer, onchymycotic skin, hyperhydrotic skin, actinic keratosis-affected skin, hirsute skin, etc.). By way of illustration but not by way of limitation, Device 600 is described in the context of epilation. The described device can also be used for therapeutic treatments.

Dimensions of the layers may vary according to the desired size of the final device and intended use. For example, a smaller device may be useful for the treatment of skin of the face, head or ears (e.g., epilation of facial hair), while a larger device may be useful for treatment of other areas of skin such as the legs, back and arms. In some embodiments, the layers may be substantially similar in size and shape. By way of example but not by way of limitation, the dimensions of each layer may be from about 2 millimeters to about 50 millimeters (mm) in length and/or height, and from about 0.025 mm to about 3 mm in thickness (each layer). In some embodiments, the dimensions are from about 5 mm to about 40 mm in length and/or height, from about 10 to about 30 mm in length and/or height, from about 15 to about 20 mm in length and/or height, from about 20 to about 50 mm in length and/or height or from about 30 to about 40 mm in length and/or height. In embodiments, the thickness of each layer may be from about 0.050 to about 2.5 mm thick, from about 0.075 to about 2.0 mm thick, from about 1 to about 1.75 mm thick or from about 1.25 to about 1.50 mm thick. The dimensions of each layer, in length and height, may be the same or different, the dimensions of thickness of each layer may be the same or different (e.g., the thickness of each layer may very due to manufacturing constraints, or may be intentionally varied, for example, by plus or minus 10% to about 50%), and each layer of a device may have the same or different dimensions. Exemplary dimensions are also provided for some of the layers in FIG. 14A, discussed below.

Figure 14A:
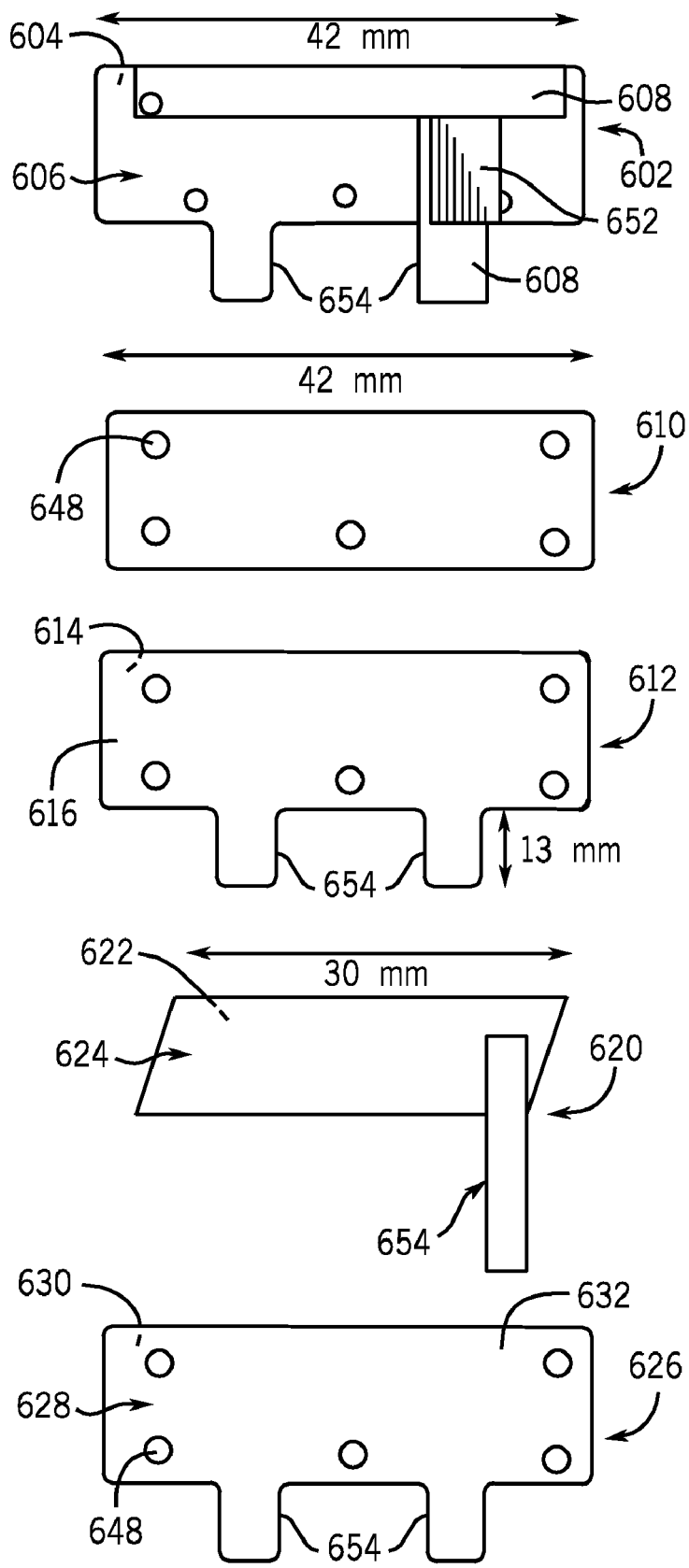
FIGS. 14A-H are schematic depictions of a device of the present invention that is substantially a laminated device.
Figure 14A:
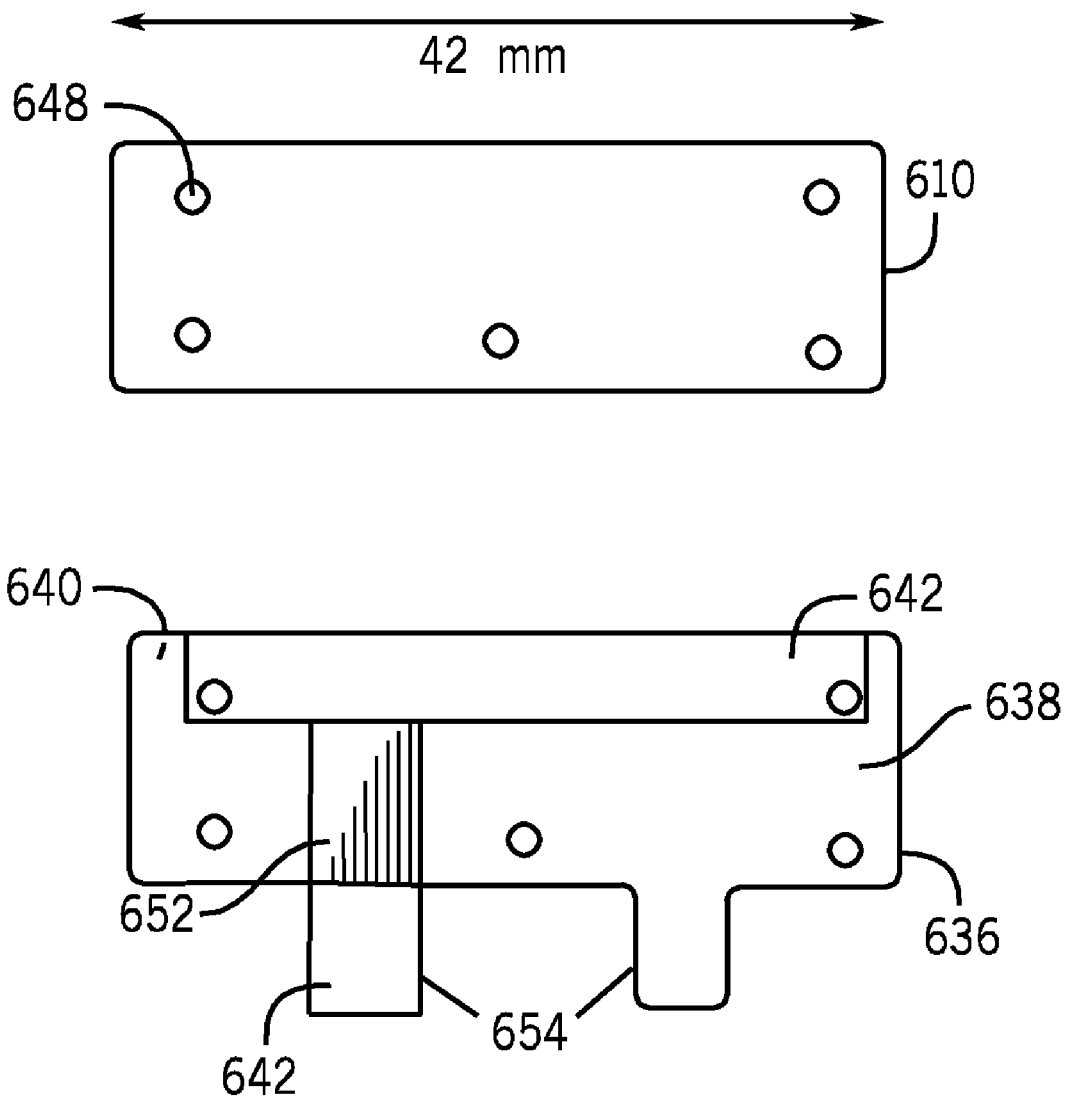

FIG. 14A illustrates one embodiment of the device, with the individual layers displayed. In FIG. 14A, only one side of each layer is visible. In some embodiments, the layers may be stacked, one on top of the other. One stacking configuration that was constructed and tested, from top to bottom, is as follows.

A first negative electrode layer 602. One example of a first negative electrode layer 602 comprises a non-conductive top surface 604 and a conductive bottom surface 606. For example, the first negative electrode layer 602 shown in FIG. 14A was formed from a polyester film, and the first negative electrode 608 was printed on the bottom surface 606 using conductive printable ink. However, a first negative electrode layer 602 can be formed from any number of materials that are non-conductive or dielectric, and are compatible with conductive, printable inks. Such materials include but are not limited to plastic, epoxy, polyvinylchloride (PVC), polyester and glass. Non-limiting examples of conductive inks include EP-5600 Silver Epoxy ink (From Ercon, Mass. USA), E1400 chlorinated polymer silver ink (From Ercon, Mass. USA), E1400, AG-500 Silver Ink (Conductive Compounds Londonderry), modified chlorinated polymer carbon/graphite E3456 (From Ercon, Mass. USA). Additionally or alternatively, the first negative electrode 608 may be joined to the bottom surface 606 by any number of methods known in the art. For example, the first negative electrode 608 could be mechanically or chemically joined to the bottom surface 606, with pins, by welding or with adhesive.

A conduit layer 610. The conduit layer 610 may be a salt bridge. As used herein, the terms "salt bridge," "agar bridge" and "ion bridge" are used interchangeably. One example of a salt bridge conduit layer comprises a salt and a substrate. For example, the conduit layer 610 shown in FIG. 14A was formed from paper (a support) that had been submerged in a hot, saturated solution of NaCl (salt) with 3% agarose (a substrate). However, a conduit layer 610 may include different percentages of substrate such as agarose (e.g., from about 1% agarose to about 10% agarose, from about 2% agarose to about 8% agarose, from about 3% agarose to about 7% agarose, from about 4% agarose to about 6% agarose or about 5% agarose) and/or may include different salts or combinations of salts (e.g., KCl, LiCl, $Na_2HPO_4$, and $CaCl_2$). In further embodiments, different concentrations of salts may be used. For example, a salt solution may be about 10% saturated, about 20% saturated, about 30% saturated, about 40% saturated, about 50% saturated, about 60% saturated, about 70% saturated, about 80% saturated, about 90% saturated or about 95% saturated. In some embodiments, material other than agarose may be used as substrate. For example, agar, polyacrylate, gelatin, alginate-Ca and other materials that, in combination with water and a salt, can become gel-like or semi-solid are suitable substrates. Additional, non-limiting examples of conduit support materials include fabrics, non-woven materials, cotton, plastic tubing and mesh.

A first positive electrode layer 612. One example of a first positive electrode layer 612 comprises a conductive top surface 614, and a non-conductive bottom surface, 616, which includes a first positive electrode, 618. By way of example, but not by way of limitation, the first positive electrode layer 612 of FIG. 14A was made with a non-conductive substrate that is resistant to oxidation, and a first positive electrode, 618, was printed on the entire top surface 612 using a conductive, printable ink. Similar to the first negative electrode layer, the first positive electrode layer may be made of other materials. For example, the substrate layer may comprise materials which are non-conductive or dielectric and which are compatible with the conductive ink, such as those described above for the first negative electrode layer. Additionally or alternatively, the electrode 618 may be joined to the top surface 614 by any number of methods known in the art, such as those described above for the negative electrode layer. Similarly, the substrate of the first positive electrode layer 612 may comprise any suitable inert material known in the art such as epoxy, PVC, polyester, and glass.

A second negative electrode layer 620. One example of a second negative electrode layer comprises a conductive top surface 622 and a conductive bottom surface 624. In FIG. 14A, the second negative electrode layer, 620, was made of a conductive material (e.g., silver, gold, platinum or other conductive metal). Alternatively, the second negative electrode layer 620 may comprise an inert substrate and the conductive surfaces 622 and 624 may comprise electrodes. Optionally, the second negative electrode layer may include a conductive cover such as metal, for example, silver, gold stainless steel or a combination thereof, or conductive ink. Optionally, the second negative electrode layer 620 may be smaller in size compared to the other electrode layers. Exemplary dimensions for a positive electrode layer and a second negative electrode layer are provided in FIG. 14A.

A second positive electrode layer 626. The second positive electrode layer, 626, has a conductive bottom surface 628 and a non-conductive top surface 630. Similar to the first positive electrode layer, 612, the second positive electrode layer 626 shown in FIG. 14A was made of a non-conductive substrate with a second positive electrode 632 printed on the bottom surface 628. Additionally or alternatively, electrode 632 may be mechanically or chemically joined to the bottom surface

628, and the substrate may be any suitable non-conductive or dielectric material, such as describe for the first positive electrode layer, 612.

A conduit layer 610.

A third negative electrode layer 636. The third negative electrode layer 636 has a conductive top surface 638 and a non-conductive bottom surface 640, the conductive top surface 638 including a third negative electrode 642. Similar to the first negative electrode layer 602, the third negative electrode layer 636 may comprise a polyester film or other inert material, and have a negative electrode 642 printed (or otherwise joined) to the conductive top surface, 638.

In some embodiments, one or more of the electrode layers may be made of metal instead of inert films, plastics, etc. The device configuration is essentially the same, but the electrode manufacturing technology is different. In such embodiments, the substrate is a metal (e.g., gold, silver, platinum, stainless steel, etc.) and instead of printing an electrode onto a dielectric film, parts of the metal intended to be non-reactive are covered (e.g., insulated). The exposed metal is the reactive electrode.

Referring to the first and third negative electrode layers 602 and 636, an insulating layer 652 is positioned to cover a portion of the first negative electrode 608 and the third negative electrode 642. Such an insulating layer may be made up of any dielectric, nylon, PVC, plastic, polyethylene, glass, insulating varnish, lacquer, shellac, and other materials known in the art.

In some embodiments, all of the electrode layers include at least one arm, 654. When the electrode layers are assembled in a stack, one of the arms of each electrode layer in the stack may be used as a contact for a power supply. FIG. 15 shows one example of how the electrode layers may be connected to a power supply via the arms 654.

Figure 14B:
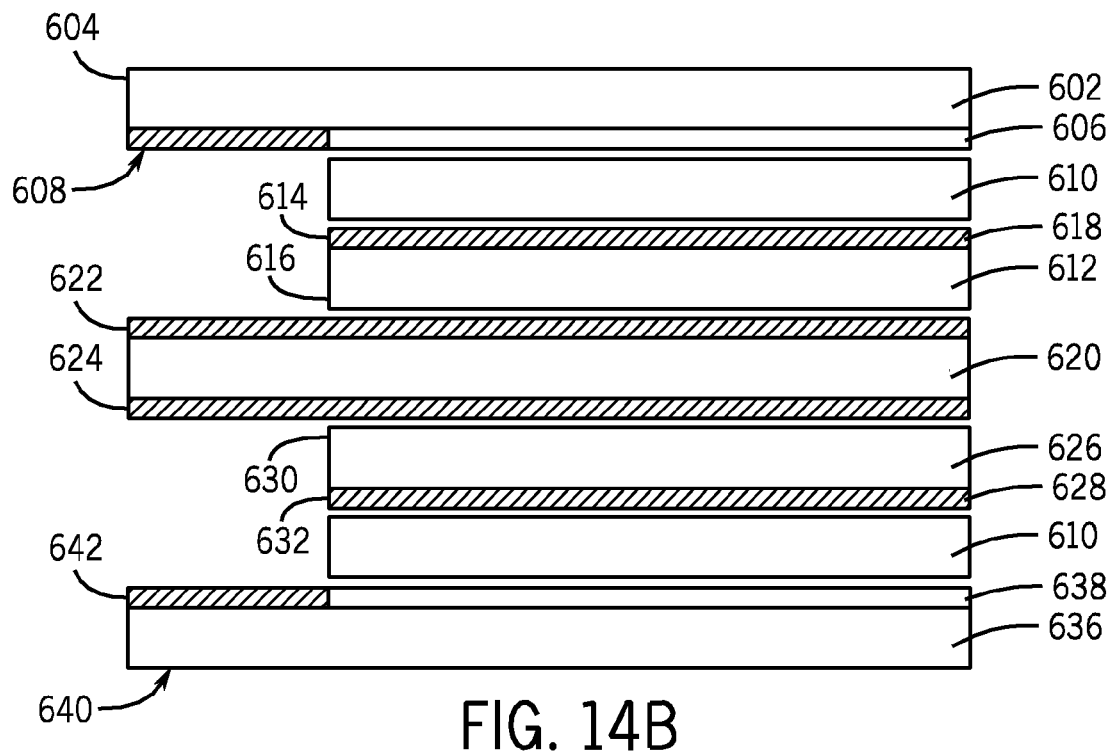

A different perspective of the Device 600 is shown in FIG. 14B. FIG. 14B shows a cross sectional view of the layers, from top to bottom (with exemplary conductive surfaces in cross-hatching): the bottom, conductive surface 606 of layer 602 showing a portion of first negative electrode 608; conduit layer 610; first positive electrode layer 612 with conductive top surface 614, positive electrode 618, and non-conductive bottom surface, 616; second negative electrode layer 620 with conductive top and bottom surfaces 622 and 624, respectively; second positive electrode layer 626 with non-conductive top surface 630, conductive bottom surface 628 and positive electrode 632; conduit layer 610; and the conductive top surface 638 of third negative electrode layer 636 showing a portion of third negative electrode 642.

Figure 14C:
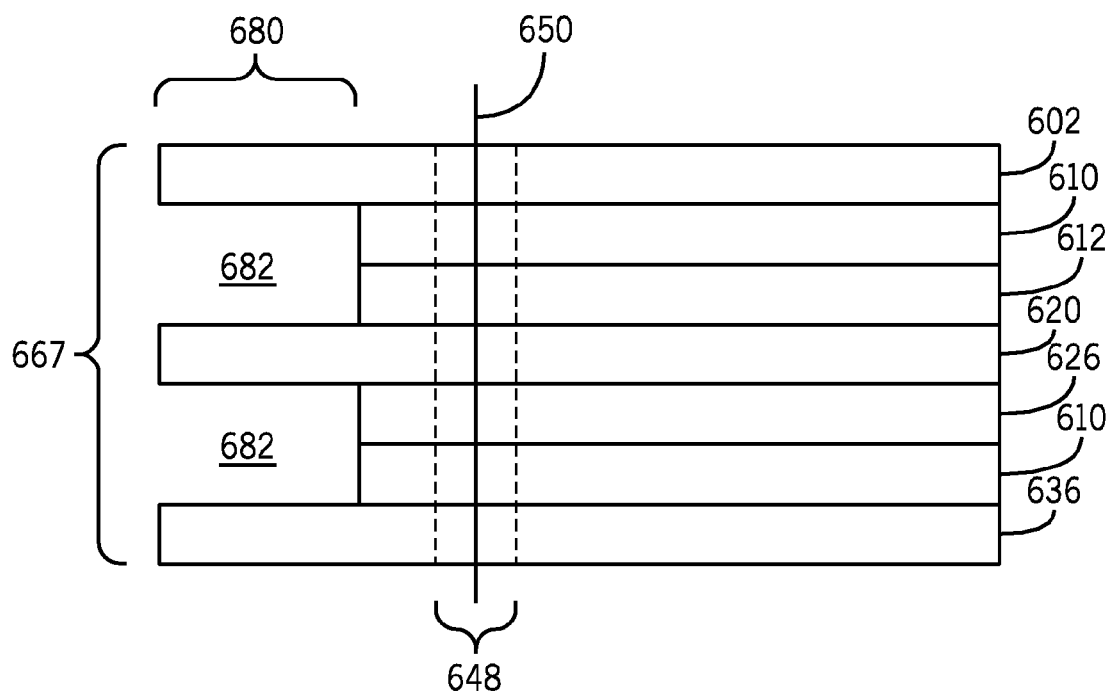

In FIG. 14C, one exemplary means of securing the layers together is shown. Holes, 648, are shown positioned to align on the different layers when the layers are stacked. Pins, 650 extend through the holes and are used to secure the different layers together. Holes, 648 are also labeled on some of the layers in FIG. 14A. Other mechanical and/or chemical means may be used to secure the layers together, for example, screws, adhesive, and chemical welding.

Referring again to FIG. 14C, at the front face of the stack of electrodes, 667, the negative electrode layers 602, 620 and 636, extend beyond the positive electrode layers 612, 626, and the conduit layers 610. This extension is shown as 680. This extension of negative electrodes results in the formation of a space between the negative electrodes, 682. In some embodiments, such a space may comprise a product reservoir; in other embodiments, such a space may form part of the product reservoir (see e.g., FIG. 14D, discussed below).

In some embodiments, the Device 600 is configured such that the front face 667 of negative electrodes 602, 620 and 636 are from about 0 to about 100 microns (µm) from the skin. In other embodiments, the front face 667 of negative electrodes 602, 620 and 636 are from about 10, from about 20, from about 30, from about 40, from about 50, from about 60 from about 70, from about 80, from about 90 or from about 100 µm from the skin.

Optionally, surrounding the layers 602-636 are an insulating layer, 644, and an outer layer, 646 (e.g., collectively termed a housing). The insulating layer 644 can be made of an insulating film such as polyester, PVC, vinyl, plastic, polyester, nylon, and polyethylene. The outer layer 646 can be made of aluminum foil, gold, silver, platinum, stainless steel and combinations thereof. Dimensions of the insulating layer 644 and the outer layer 646 may vary according to intended use and size of the electrode stack. For example, each layer may be from about 2 to about 10 millimeters thick, or from about 2-5 millimeters thick. In some embodiments, the thickness of each layer may vary.

In embodiments, the Device 600 is configured such that the front face 667 of negative electrodes 602, 620 and 636 are from about 5 to about 100 µm from the insulating layer 644. In other embodiments, the front face 667 of negative electrodes 602, 620 and 636 are from about 10, from about 20, from about 30, from about 40, from about 50, from about 60 from about 70, from about 80, from about 90 or from about 100 µm from the insulating layer 644.

Figure 14D:
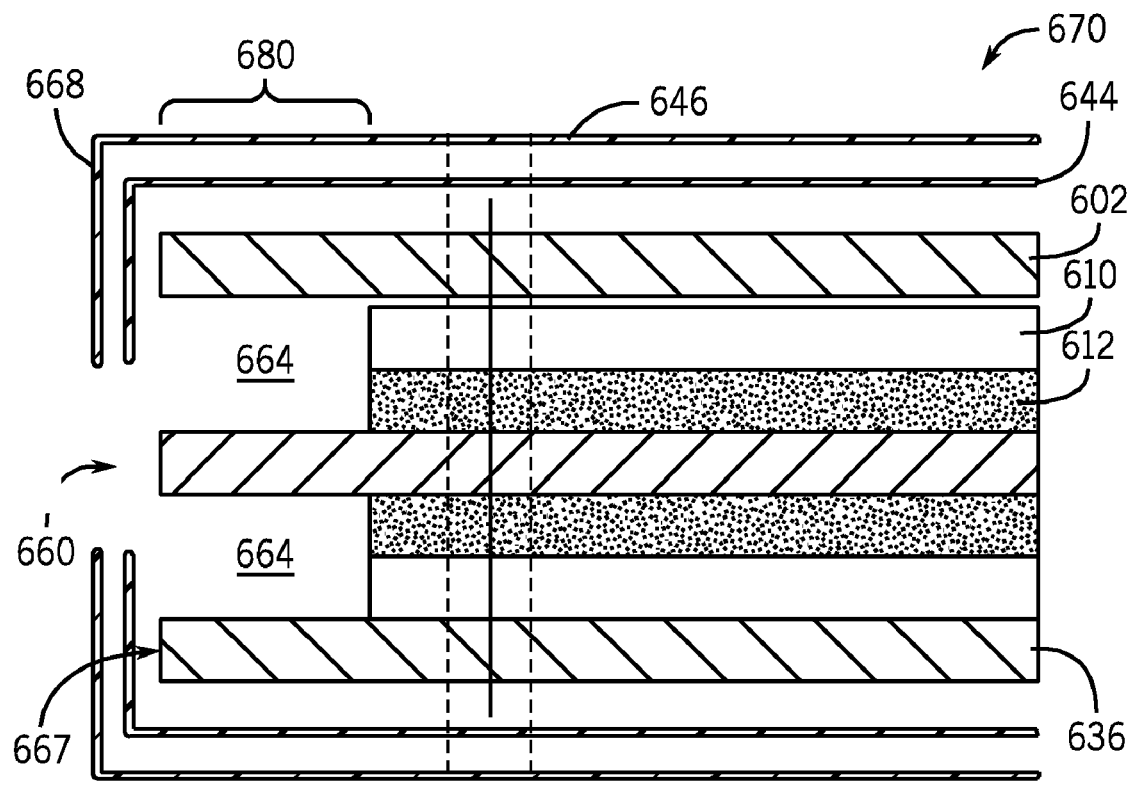
Figure 14E:
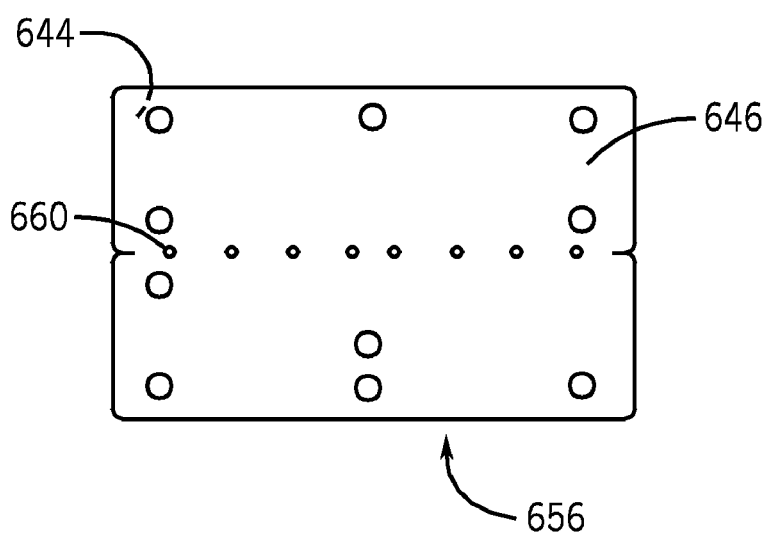

Structure 656 of FIG. 14E illustrates one embodiment of the outer layer, 646 and the insulating layer 644. The top surface 646 of structure 656 is the outer layer, while the bottom surface is the insulating layer, 644. In one embodiment, structure 656 is folded along the midline holes, 660 and positioned around the stacked electrodes. One of these holes 660, is show in the cross section view in FIG. 14D.

Referring to FIG. 14D, in embodiments including a housing, a product reservoir 664 may be formed by the space defined approximately by the insulating layer 644, the front face of the stacked electrodes 667, and the holes (apertures) 660 in the contact surface 668. In embodiments, fluid, such as electrolytic fluid, water, water and surfactant, API, etc. enter the product reservoir 664 via holes 660, and electrolytic product exits the product reservoir 664 via holes 660.

In FIG. 14D, Device 600 is shown with a contact surface 668, and a rear portion 670. In some embodiments, a handle may be affixed to the rear portion 670. In other embodiments, the handle includes a power supply, such as a direct current power supply. In still other embodiments, the Device 660 may include a power inlet in the rear portion for connection to a power supply, such as a DC power supply.

Figure 14F:
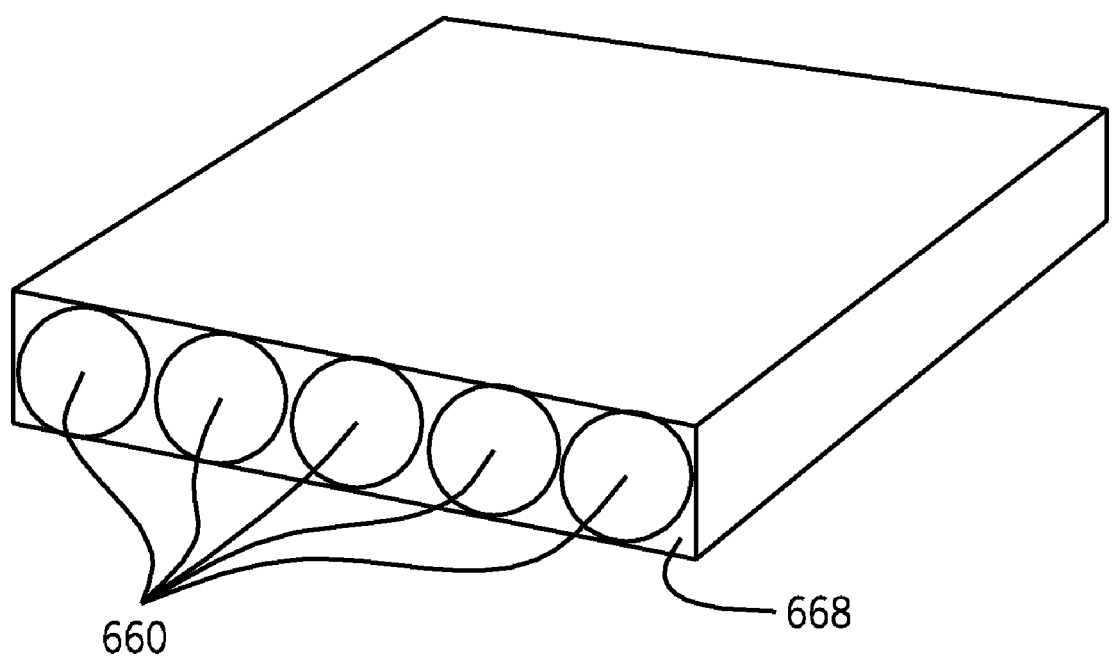

FIG. 14F shows a front view of the contact surface 668, of one embodiment of Device 600. Holes 660 in the contact surface 668 allow fluid to flow in and out of the Device 600.

In use, electrical power, such as direct current electrical power, is supplied to the contact. The contact surface 668 of device 600 is dipped in fluid, such as water or water and surfactant, and the contact surface 668 is positioned proximate to the skin. In embodiments, the contact surface contacts the skin. Front face of the stacked electrodes 667, particularly the extended portions of the negative electrode layers 680 are proximate to the holes 660 and to the skin. Generally, the negative electrode front faces are about 50-100 µm from the skin. Fluid enters holes, 660. In embodiments, the fluid combines with salt from the conduit layers 610, resulting in an electrolytic fluid. In embodiments, electrochemical reactions occur in the electrolytic fluid in the presence of current. In embodiments, the fluid is water. In embodiments, the conduit 610 is highly conductive in the presence of fluid. In embodiments the conduit 610 is an ion bridge. In embodiments, the conduit closes or completes a circuit (e.g., an electrochemical system) between electrodes (e.g., between a first negative electrode and a first positive electrode), allowing electrochemical reactions to occur in the presence of current. In embodiments, the electrochemical reactions occur in an electrolytic fluid.

In embodiments without a housing, the Device 600 may be used substantially as described above. The front face 667 of negative electrodes, 602, 620 and 636 is dipped in fluid. In embodiments, the front face 667 of negative electrodes 602, 620 and 636 is positioned proximate to the skin. In other embodiments, the front face 667 of negative electrodes 602, 620 and 636 contacts the skin.

As described above for device 544, it is believed that the electrolysis of components of the electrolytic fluid generate electrolysis products such as $OH^-$ ions and $H_2$ gas. Such products are generated in or near the product reservoir, 664, at the front face 667 of the stacked electrodes. Due to the construction of the device, the electrolysis occurs in a small volume of fluid, resulting in a high concentration of electrolysis products. It is believed that the combination of electrolysis products and surfactant results in the formation of bubbles. The bubbles exit the holes 660, and move the products of electrolysis to the skin. The concentration of electrolytic products is high enough so that sufficient products migrated through holes 660 to damage the hair roots and consequently lead to epilation. Due to the very low voltages used, the movement of products out of the device in the presence of the bubbles is faster than diffusion and the electrophoretic movement of products resulting from the weak electric field.

Generally, effective epilation occurs when the pH of the electrolytic products (e.g., electrolytic product and other fluid(s) exiting the holes of the housing and contacting the subject's skin) is between about 10 to about 14. In embodiments, effective epilation occurs when the pH of the electrolytic products is between about 10 and about 11, between about 10 and about 12, between about 10 and about 13, between about 11 and about 13, between about 11 and about 14, between about 12 and about 14, or between about 13 and about 14. Lower pH (e.g., lower than about 10), tends to result in less effective epilation. In embodiments, the pH of the electrolytic products being produced is maintained while electrical power is supplied to the Device 600.

In embodiments, power is supplied to Device 600 via a power supply. The power supply may be a DC power supply or an AC power supply. In embodiments, the power supply is configured to provide an electric current from about 60 mA to about 600 mA, from about 100 to about 600 mA, or from about 100 to about 250 milliamps (mA). In embodiments, the power supply is configured to provide electrical power having a potential of at least 1V, at least 1.5V, at least 4.5V, at least 6V or at least 9V. In particular embodiments, about 250 mA and about 6 volts is provided. In some embodiments, a power supply is provided in a handle.

Figure 14G:
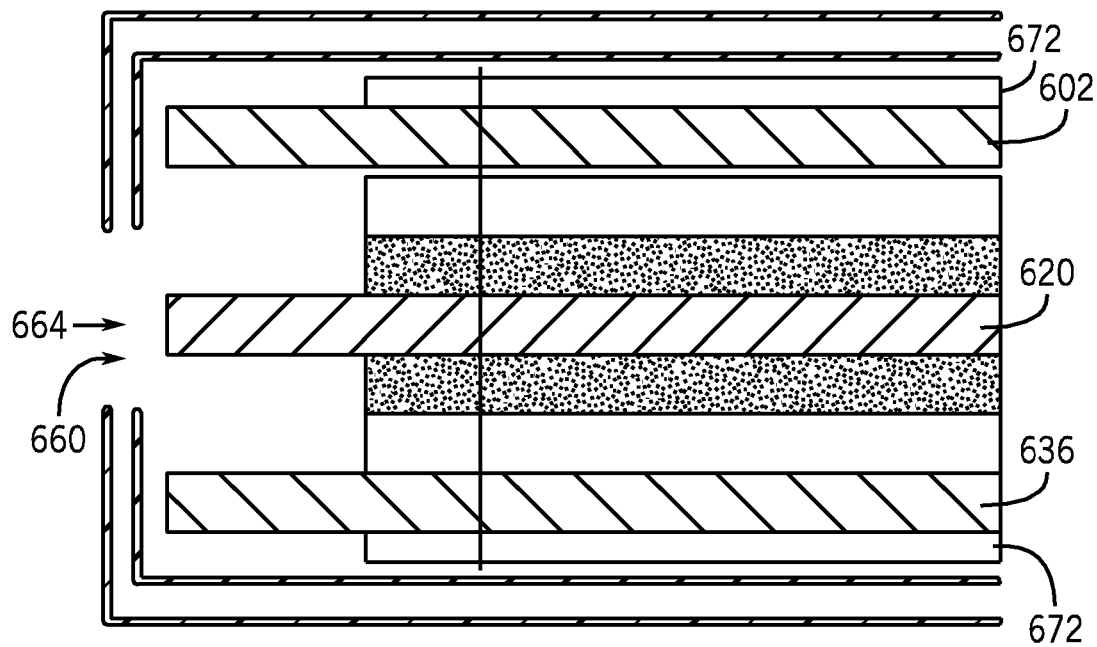

In some embodiments, surfactant or other compounds or substances may be supplied with the Device 600. As shown in FIG. 14G, surfactant is provided via one or more supply reservoirs, 672. An exemplary supply reservoir may comprise one or more pads, which include a dry or dried surfactant. When fluid enters holes 660 and contacts the supply reservoir 672, the supply reservoir 672 releases surfactant which can enter the product reservoir 664. Additionally or alternatively, active pharmaceutical ingredients (e.g., epilation active pharmaceutical ingredients) or other substances (e.g., anti-mycotic agents, anti-cancer agents, anti pre-cancer agents, sweat gland dessicant, etc.), may be provided in one or more supply reservoirs 672, as the Device 600 is useful for treatments other than just epilation.

In some embodiments, the Device 600 includes a razor. For example, the Device 600 can be manufactured to clip onto a conventional razor. Additionally or alternatively, the Device 600 may include a razor or razor blade. In embodiments, one or more of the negative electrodes may be formed as a razor blade. In use, the Device 600 is stroked along the skin, with epilation (e.g., damage of the cells responsible for hair growth) occurring substantially simultaneously with shaving the hair. In embodiments including a housing, the razor blade may be affixed or operably secured to the housing. For example, the razor or razor blade may be secured to the outside of the housing, or to the inside of the housing with an aperture formed in the contact surface to allow the blade to contact the subject's hair.

As described above, alternative embodiments of the Device 600 may be include more or fewer layers. For example, in some embodiment, multiple stacks of electrodes may used. The stacks of electrodes may be lined up (e.g., side-by-side, or adjacent to each other) or stacked (e.g., one on top of the other), with the front face 667 of each stack facing the same direction. In embodiments including a housing, the front face of the stacks 667 are proximate to the holes 660 in the contact surface, 668, and face the holes, 660.

Figure 14H:
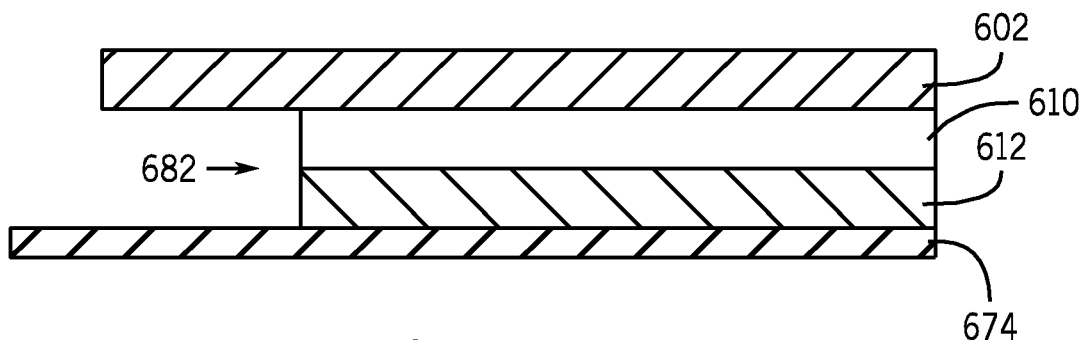

Alternative embodiments may include fewer layers. For example, a device may comprise a first negative electrode layer 602 and a first positive electrode layer 612, as described above, with a conduit 610 between these electrode layers. Optionally, an insulating layer 674 may be provided on the top surface of the positive electrode as shown in FIG. 14H. In this embodiment, reservoir 682 is created in the space between the first negative electrode layer 602 and the insulating layer 674. Optionally, one or more supply reservoirs, housing layers, a handle, razor, razor blade, and power inlet, may be added to any of the described embodiments.

FIG. 15 shows one embodiment of a power supply connection to the electrode layers of Device 600.

As discussed above, a goal of the teachings of the present invention is to generate a high number of ions in a small volume of liquid in proximity to a treated surface so as to have a high ion concentration and consequently a high efficacy of treatment. At the same time, it is desired to avoid passage of current through the body of the person being treated.

As a result, when implementing the teachings of the present invention there are a number of challenges that must be considered.

One challenge relates to the passage of current through the body of a person being treated. As is seen from the figures and described herein, the shortest electrical path and consequently path with lowest resistance is directly between a first electrode and a second electrode through the electrolytic liquid. That said, usually there exist a number of alternate electrical paths that pass from the first electrode to the body of the person through the electrolytic liquid, through the body, and from the body to the second electrode through the electrolytic liquid. As such paths are long and the resistance through the body is relatively high, the resistance of such electrical paths is much higher than the direct electrical path between the first electrode and the second electrode but is still low enough that a sufficiently high portion of the current passes through the body causing pain. In order to reduce or totally eliminate pain during use of a device of the present invention, it is desirable to lower the resistance of the direct electrical path between the first and second electrodes and increase the resistance of alternative electrical paths.

Therefore, in embodiments the area of the conduit when emerging from the contact surface is small so as to increase the electrical resistance through the electrolyte. Typically, dimensions of a conduit opening are no more than about 100 micrometers. In embodiments, the conduit opening is substantially one or more small perforations or such openings having a diameter of no more than about 100 micrometers (or a substantially equivalent area if not round). In embodiments, the conduit opening is substantially a slit no more than about 100 micrometers broad, for example a slit that is 100 micrometers broad and between 2 cm and 6 cm wide.

That said, in order to allow for a greater current in order to produce more electrolysis products without excess heating of the electrolysis fluid, it is preferred that the resistance of the electrical path between the first electrode and second electrode be as low as possible, that is to say short and having a large cross section.

Embodiments of devices of the present invention, including devices 500, 524, 530, 544 and 600 described above are useful for implementing embodiments of a method for topical treatments of skin of the present invention. In the method, a face of a first electrode is positioned proximate to the skin (no more than about 2 mm, no more than about 1 mm, no more than about 0.5 mm and even substantially contacting the skin, for example through a thin film of electrolytic fluid), a face of a second electrode is positioned so that an electrical path between the faces of the electrodes does not pass through the body, the first and second electrodes are brought in electrical contact through an electrolytic fluid; and a current is passed through the electrode faces and electrolytic fluids so as to generate products of electrolysis of components of the electrolytic fluid in the proximity of the face of the first electrode, where the electrolysis products are useful in achieving a desired effect, as discussed herein.

Although devices 500, 524, 530, 544 and 600 are discussed for use with a NaCl solution for hair removal where a first electrode (or first set of electrodes), for example, electrode 508 (or electrodes 602, 620 and 636) is an anode, any of the reactants, reactant containing solutions and electrolytic fluids discussed herein are also useable with the appropriately modified devices and where a first electrode 508 (or 602, 620 and 636) is a cathode.

Biological Applications

Before explaining additional biological applications of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

This invention has multiple biological applications well beyond those presented, the many additional applications and/or modifications to the invention for each application being known to those familiar with the art.

Electro-Hair Removal

Referring to FIG. 1, as noted above, hair 204 grows from a follicle 208, which is not fully keratinized and therefore rapidly absorbs electrolytic products.

Reactant 184 comprises, for example, a salt of NaCl or KCl. (OH$^-$) ions from reactant 144 form at electrode (−) 130, while (H+) acid forms at electrodes (+) 110. In an exemplary embodiment, follicle 208 absorbs (OH$^-$) ions from reactant 144 that are in liquid form, thereby causing poisoning of follicle 208.

Only a small amount of (OH$^-$) ions from reactant 144 is needed, due to the small size of follicle 208. The high pH gradient is maintained as long as the electrochemical reaction takes place. The speed of reaction, for example, can be reduced by adding a buffer to reactant 184.

Device 600 also functions in epilation. Similar to the device of FIG. 1, (OH−) ions from at the negative electrodes of negative electrode layers 602, 620 and 636, while (H+) ions form at the positive electrodes of positive electrode layers 612 and 626. In embodiments, the hair follicle (such as shown in FIG. 1 at 208), absorbs (OH−) ions released to the skin.

In an alternative embodiment, a needle extending from electrode (−) 130 having a similar structure to the 2-ECD 800, FIG. 8, is placed relatively close to follicle 208 to cause ionic changes within follicle 208 without the intermediary of reactant 184.

In an exemplary electrolysis embodiment, nose 820 is sharp to facilitate entry into tissue and opening 164 is positioned near or within pointed nose 820. Optionally, pad 146 contains reactants 145 that produce OH$^-$ and $H_2$.

Poisoning of follicle 208 with OH$^-$ appears to occur in the anagen and telogen phases, but not in catagen phase. However, it is likely that a catagen phase follicle 208 is likely to be poisoned by delivering an appropriate electrolytic product 144 other than OH$^-$; with dual products 144 being readily delivered by a 2-ECD 800 as described above. Thus, using 2-ECD 800 or other embodiments, treatment of all three phases of follicular 208 growth could arrested in a single treatment.

Onychomycosis

Using System 200 (FIG. 1), treatment of onychomycosis following nail avulsion would use an appropriate topical reactant comprising a standard topical anti-mycotic agent, for example: amorolfine, ciclopirox olamine, sodium pyrithione, bifonazole/urea, propylene glycol-urea-lactic acid, imidazoles, or allylamines. To facilitate a well-focused and deep deposition that is appropriate for the nail fold, base 148 and insulating layer 174, in addition to the shaped opening 164 noted above, comprise a curvature and/or a flexible material to ensure conformation to the nail layer curvature.

While the above-noted treatment has not been performed, it is postulated that 2-ECD 143 will facilitate efficient intracellular deposition of product 145 so that treatments can be limited to once a week until the nail appears clear of infection.

Embodiments of the Device 600 could also be used to treat onychomycosis. For example, by providing the appropriate agent in one or more supply reservoirs 672, and shaping the contact surface 668 of the housing to form to the nail curvature, effective treatment could be provided.

Hyperhydrosis

System 400 (FIG. 7) is optionally used in treating multiple tissue types for the purpose of treating primary hyperhydrosis.

While at the present time, the most efficacious combination of current, voltage and/or pulse width is unknown, system 400 provides the option of providing two different electrical currents and/or electrolytic reactants 145, a first tailored to affect eccrine glands and a second tailored to affect apocrine glands; thereby greatly increasing effectiveness in addition to the exceptional speed of 4-ECD 195.

Additionally, it is postulated that 3-ECD 140, with AC side electrode 120, has the potential to also affect multiple types of tissue 188.

Embodiments of the Device 600 could also be used to treat hyperhydrosis. For example, by providing a hyperhydrosis API in one or more supply reservoirs 672 and positioning the contact surface 668 proximate to hyperhydrotic skin, effective treatment of the hyperhydrotic skin could be provided.

Surface Tumor Treatment

Using 3-ECD 140, a surface tumor, for example squamous cell carcinoma in situ, would likely respond to electrolytic desiccation treatments using similar techniques as those previously described for single electrode pair used in hyperhydrosis treatments.

Embodiments of the Device 600 could also be used to treat surface tumors. For example, by providing the appropriate anti-cancer agent in one or more supply reservoirs 672 and positioning the contact surface 668 proximate to cancerous skin, treatment of the cancerous skin could be provided.

It is expected that during the life of this patent many relevant delivery systems will be developed and the scope of the term AC Tissue Treatment is intended to include all such new technologies a priori.

As used herein the term "about" refers to ±10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

What is claimed is:

1. An electrically powered device for treatment of a subject's skin comprising layers of stacked electrodes, comprising:
    at least two positive electrodes;
    at least two negative electrodes, each of which extends beyond said positive electrodes such that a space between said negative electrodes is formed; said space is characterized by the accumulation of the electrolytic product formed by providing electrical power to said reactant;
    at least one conduit and a first reservoir for holding a fluid; said fluid comprising a reactant;
    at least a portion of said reactant being electrolysable; said conduit is characterized by having at least one opening;
    each of said conduits are being positioned intermediate one of said negative electrode and one of said positive electrode,
    said conduits being formed of a material that completes a circuit between said negative electrodes and said positive electrodes when said conduits are in communication with said reactant;
    at least one adhesive layer positioned in between each two electrodes;
    wherein said at least one opening in said conduit is characterized by having diameters not greater than 100 micrometers so as to increase the electrical resistance through the electrolyte so as to provide the direct electrical path between the electrodes with the lowest electrical resistance.

2. The device of claim 1, wherein treatment comprises epilation, and wherein said conduit is formed of a material that provides the electrolytic fluid when in contact with the fluid.

3. The device of claim 2, wherein said conduit comprises a substrate and a salt.

4. The device of claim 3, wherein the salt comprises sodium chloride, and wherein said substrate is selected from the group consisting of agarose, agar, polyacrylate, gelatin, alginate-Ca, and combinations thereof.

5. The device of claim 1, further comprising:
    a second negative electrode and a third negative electrode formed as plates, the second negative electrode being conductive on both sides, the third negative electrode having a conductive side and a non-conductive side;
    a second positive electrode formed as a plate and having a conductive side and a non-conductive side;
    a second conduit;
    the first negative electrode having a conductive side and a non-conductive side; and
    the first positive electrode having a conductive side and a non-conductive side;
    the electrodes and the first and second conduit forming a substantially laminate construct configured to produce hydroxide ions in the first reservoir when electrical power is provided to the electrolytic fluid.

6. The device of claim 1, wherein the fluid comprises water and a surfactant.

7. The device of claim 6, wherein the surfactant forms bubbles in the first reservoir when electrical power is provided, and wherein the hydroxide ions exit said reservoir through the at least one contact surface aperture with the bubbles.

8. The device of claim 1, further comprising a razor operably secured to the housing.

9. The device of claim 1, wherein at least one of said negative electrode comprises a razor blade.

10. The device of claim 1, further including a reservoir comprises a void.

11. The device of claim 1, wherein said reservoir comprises an absorbent material.

12. The device of claim 1, wherein said conduit is a capillary conduit.

13. The device of claim 1 wherein said conduit comprises a capillary passage.

14. The device of claim 1, wherein said conduit comprises a tangible material configured for capillary transport of said electrolytic fluid.

15. The device of claim 1, wherein said conduit has a first face and an opposing second face, the first negative electrode being proximate the first face of the conduit and the first positive electrode being proximate the second face of the conduit.

16. The device of claim 1, wherein the conduit has a first face and an opposing second face, the first negative electrode being proximate the first face of the conduit and the first positive electrode being proximate the second face of the conduit.

17. The device of claim 1, wherein said electrodes are formed as plates.

18. The device of claim 1, wherein said stack of electrodes are lined up (side-by-side) or stacked one on top of the other.

19. The device of claim 1, wherein at least one of said negative or positive electrode is characterized by at least one selected from a group consisting of being conductive on both sides, having a conductive side and a non-conductive side.

20. The device of claim 19, wherein at least one of said electrodes and said conduit forming a substantially laminate construct configured to produce hydroxide ions in said reservoir when electrical power is provided to the electrolytic fluid.

21. A method for treating a subject's skin comprising:
   providing an electrically powered device, comprising layers of stacked electrodes, comprising
   at least two positive electrodes;
   at least two negative electrodes, each of which extends beyond said positive electrodes such that a space between said negative electrodes is formed; said space is characterized by the accumulation of the electrolytic product formed by providing electrical power to said reactant;
   at least one conduit and a first reservoir for holding a fluid; said fluid comprising a reactant; at least a portion of said reactant being electrolysable; said conduit is characterized by having at least one opening;
   each of said conduits are being positioned intermediate one of said negative electrode and one of said positive electrode,
   said conduits being formed of a material that completes a circuit between said negative electrodes and said positive electrodes when said conduits are in communication with said reactant;
   at least one adhesive layer positioned in between each two electrodes;
   wherein said at least one opening in said conduit is characterized by having diameters not greater than 100 micrometers so as to increase the electrical resistance through the electrolyte so as to provide the direct electrical path between the electrodes with the lowest electrical resistance;
   positioning a portion of the first negative electrode proximate to the subject's skin;
   positioning the conduit intermediate the first positive electrode and the first negative electrode;
   contacting the first negative electrode, the first positive electrode and the conduit with a fluid, wherein contacting the conduit with the fluid provides a circuit between the first negative electrode and the first positive electrode;
   providing an electrolytic fluid in communication with the first positive electrode and the first negative electrode;
   providing an electrical current between the first positive electrode and the first negative electrode through the electrolytic fluid;
   forming electrolytic products proximate to the portion of the first negative electrode proximate to the subject's skin; and
   releasing the electrolytic products to the subject's skin.

22. The method of claim 21, wherein the conduit is formed of a material that provides the electrolytic fluid when in contact with the fluid.

23. The method of claim 22, wherein the fluid comprises water, and wherein the conduit comprises, a substrate and a salt.

* * * * *